US012579244B2

(12) United States Patent
    Chang

(10) Patent No.:    US 12,579,244 B2
(45) **Date of Patent:    \*Mar. 17, 2026**

(54) SHARED VIRTUAL REALITY SYSTEM USING WEARABLE ACCESSARY

(71) Applicant: PixArt Imaging Inc., Hsin-Chu County (TW)

(72) Inventor: Yen-Min Chang, Hsin-Chu County (TW)

(73) Assignee: PIXART IMAGING INC., Hsin-Chu County (TW)

( \* ) Notice: Subject to any disclaimer, the term of this patent is extended or adjusted under 35 U.S.C. 154(b) by 107 days.

This patent is subject to a terminal disclaimer.

(21) Appl. No.: 18/636,325

(22) Filed: Apr. 16, 2024

(65) Prior Publication Data

US 2024/0265082 A1    Aug. 8, 2024

Related U.S. Application Data

(63) Continuation-in-part of application No. 18/222,008, filed on Jul. 14, 2023, now Pat. No. 11,989,274, (Continued)

(30) Foreign Application Priority Data

Jul. 8, 2014    (TW) ................................. 103123544

(51) Int. Cl.
    *G06F 21/32*        (2013.01)
    *A61B 5/117*        (2016.01)
                    (Continued)

(52) U.S. Cl.
    CPC .............. *G06F 21/32* (2013.01); *A61B 5/117* (2013.01); *A61B 5/1172* (2013.01); *A61B 5/1176* (2013.01); *G06V 40/70* (2022.01); *G06V 40/12* (2022.01); *G06V 40/15* (2022.01); *G06V 40/172* (2022.01); *G06V 40/197* (2022.01); *H04L 67/131* (2022.05)

(58) Field of Classification Search
    CPC ........ G06V 40/70; G06V 40/12; G06V 40/15; G06V 40/172; G06V 40/197; A61B 5/117; A61B 5/1172; A61B 5/1176; H04L 67/131; G06F 21/32
    USPC .............................................. 726/2–5, 17–20
    See application file for complete search history.

(56) References Cited

U.S. PATENT DOCUMENTS 7,224,326 B2 \*  5/2007  Sefton ................ A63B 71/0622
                                                    345/9
9,189,901 B2 \*  11/2015  Agrafioti ................. G06F 21/32
                    (Continued)

*Primary Examiner* — Bharat Barot
(74) *Attorney, Agent, or Firm* — WPAT, PC

(57)            ABSTRACT

A virtual reality system including an image viewing device and a wearable accessary is provided. The image viewing device detects a biometric characteristic to identify a user ID according to the biometric characteristic, outputs an ID signal associated with the identified user ID and shows video stream associated with the identified user ID. The wearable accessary detects an attached status and movement of the wearable accessary after receiving the ID signal, and sends a control signal to the image viewing device to change image content in the video stream according to the detected movement of the wearable accessary when the attached status indicates continuous wearing.

20 Claims, 17 Drawing Sheets

Related U.S. Application Data which is a continuation of application No. 17/527,278, filed on Nov. 16, 2021, now Pat. No. 11,748,464, which is a continuation-in-part of application No. 16/878,225, filed on May 19, 2020, now Pat. No. 11,210,381, which is a continuation-in-part of application No. 16/716,806, filed on Dec. 17, 2019, now Pat. No. 10,699,558, which is a continuation-in-part of application No. 16/519,197, filed on Jul. 23, 2019, now Pat. No. 10,554,660, which is a continuation-in-part of application No. 16/360,605, filed on Mar. 21, 2019, now Pat. No. 10,403,060, which is a continuation-in-part of application No. 16/117,334, filed on Aug. 30, 2018, now Pat. No. 10,282,928, which is a continuation-in-part of application No. 15/964,718, filed on Apr. 27, 2018, now Pat. No. 10,089,802, which is a continuation-in-part of application No. 15/722,435, filed on Oct. 2, 2017, now Pat. No. 9,984,222, which is a continuation-in-part of application No. 15/343,509, filed on Nov. 4, 2016, now Pat. No. 9,818,245, which is a continuation-in-part of application No. 14/684,648, filed on Apr. 13, 2015, now abandoned.

(51) Int. Cl.

| | |
|---|---|
| *A61B 5/1171* | (2016.01) |
| *A61B 5/1172* | (2016.01) |
| *G06V 40/70* | (2022.01) |
| *H04L 67/131* | (2022.01) |
| *G06V 40/10* | (2022.01) |
| *G06V 40/12* | (2022.01) |
| *G06V 40/16* | (2022.01) |
| *G06V 40/18* | (2022.01) |

(56) References Cited

U.S. PATENT DOCUMENTS

| | | | |
|---|---|---|---|
| 10,867,023 B2* | 12/2020 | Yun | G06F 21/32 |
| 11,989,274 B2* | 5/2024 | Chang | A61B 5/1172 |

* cited by examiner detecting, using a detection device, a biometric characteristic — S51 comparing the biometric characteristic with pre-stored biometric characteristic information to identify a user ID — S52 performing, using a control host, an individualized control according to the user ID — S53

SHARED VIRTUAL REALITY SYSTEM USING WEARABLE ACCESSARY

RELATED APPLICATIONS

The present application is a continuation-in-part application of U.S. patent application Ser. No. 18/222,008 filed on, Jul. 14, 2023, which is a continuation application of U.S. patent application Ser. No. 17/527,278 filed on, Nov. 16, 2021, which is a continuation-in-part application of U.S. patent application Ser. No. 16/878,225 filed on, May 19, 2020, which is a continuation-in-part application of U.S. patent application Ser. No. 16/716,806 filed on, Dec. 17, 2019, which is a continuation-in-part application of U.S. patent application Ser. No. 16/519,197 filed on, Jul. 23, 2019, which is a continuation-in-part application of U.S. patent application Ser. No. 16/360,605 filed on, Mar. 21, 2019, which is a continuation-in-part application of U.S. patent application Ser. No. 16/117,334 filed on, Aug. 30, 2018, which is a continuation-in-part application of U.S. patent application Ser. No. 15/964,718 filed on, Apr. 27, 2018, which is a continuation-in-part application of U.S. patent application Ser. No. 15/722,435 filed on, Oct. 2, 2017, which is a continuation-in-part application of U.S. patent application Ser. No. 15/343,509 filed on, Nov. 4, 2016, which is a continuation-in-part application of U.S. patent application Ser. No. 14/684,648 filed on, Apr. 13, 2015 and claims priority to Taiwanese Application Number 103123544, filed on Jul. 8, 2014, the full disclosures of which are hereby incorporated by reference herein in their entirety.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

BACKGROUND

1. Field of the Disclosure

This disclosure generally relates to a control system and, more particularly, to an individualized control system utilizing a biometric characteristic and an operating method thereof.

2. Description of the Related Art

Pulse oximeters utilize a noninvasive method to monitor the blood oxygenation and the heart rate of a user. An optical pulse oximeter generally emits a red light beam (wavelength of about 660 nm) and an infrared light beam (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 entitled "Method for spectrophotometric blood oxygenation monitoring". After the intensity variations, e.g. photoplethysmographic signals or PPG signals, of the penetrating light of the two wavelengths are detected, the blood oxygenation can then be calculated according to an equation: Blood oxygenation$=100\%\times[HbO_2]/([HbO_2]+[Hb])$, wherein $[HbO_2]$ is an oxyhemoglobin concentration; and $[Hb]$ is a deoxyhemoglobin concentration.

Generally, the intensity variations of the penetrating light of the two wavelengths detected by a pulse oximeter will increase and decrease with heartbeats. This is because blood vessels expand and contract with the heartbeats such that the blood volume that the light beams pass through will change to accordingly change the ratio of light energy being absorbed. Therefore, the absorptivity of blood of different light spectra can be calculated according to the intensity information changing continuously so as to calculate PPG signals. By further analyzing the PPG signals, biometric characteristics such as the heart rate variability (HRV) and second derivative of photoplethysmogram (SDPPG) are obtainable.

In addition, another kind of electrode type biosensor monitors the biometric characteristics such as the heart rate variability (HRV), electroencephalography (EEG), galvanic skin response (GSR), electrocardiogram (ECG) and electromyography (EMG) by detecting bio-signals.

SUMMARY

The present disclosure provides a virtual reality (VR) system including an image viewing device and a wearable accessary. The image viewing device includes a VR box and a system server coupled to the VR box. The VR box is configured to detect a biometric characteristic to identify a user ID according to the biometric characteristic, and output an ID signal associated with the identified user ID. The system server is configured to receive the ID signal from the VR box, receive shared video stream sharing from another VR box coupled to the system server via an internet, and transmit video stream associated with the identified user ID or the shared video stream to the VR box to be shown thereon. The wearable accessary is configured to detect an attached status and movement of the wearable accessary after receiving the ID signal from the VR box, and send a control signal to the image viewing device to change image content to be shown on the VR box as the video stream or the shared video stream according to the detected movement of the wearable accessary when the attached status indicates continuous wearing.

The present disclosure further provides a virtual reality (VR) system including an image viewing device and a wearable accessary. The image viewing device includes a VR box and a system server coupled to the VR box. The VR box is configured to detect a biometric characteristic and output the biometric characteristic. The system server is configured to receive the biometric characteristic to identify a user ID accordingly, receive shared video stream sharing from another VR box coupled to the system server via an internet, and transmit video stream associated with the identified user ID or the shared video stream to the VR box to be shown thereon. The wearable accessary is configured to identify the user ID according to the biometric characteristic received from the VR box, detect an attached status and movement of the wearable accessary after confirming a valid user ID, and send a control signal to the image viewing device to change image content to be shown on the VR box as the video stream or the shared video stream according to the detected movement of the wearable accessary when the attached status indicates continuous wearing.

The present disclosure further provides a virtual reality (VR) system including an image viewing device and a wearable accessary. The image viewing device includes a VR box. The VR box is configured to identify a user ID and output an ID signal associated with the identified user ID, be coupled to an internet to receive shared video stream sharing from an imaging device connected to the internet, and show video stream associated with the identified user ID or the shared video stream thereon. The wearable accessary is configured to detect movement of the wearable accessary after receiving the ID signal from the VR box, and send a control signal to the image viewing device to change image content to be shown on the VR box as the video stream or the shared video stream according to the detected movement of the wearable accessary.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

Figure 1A:
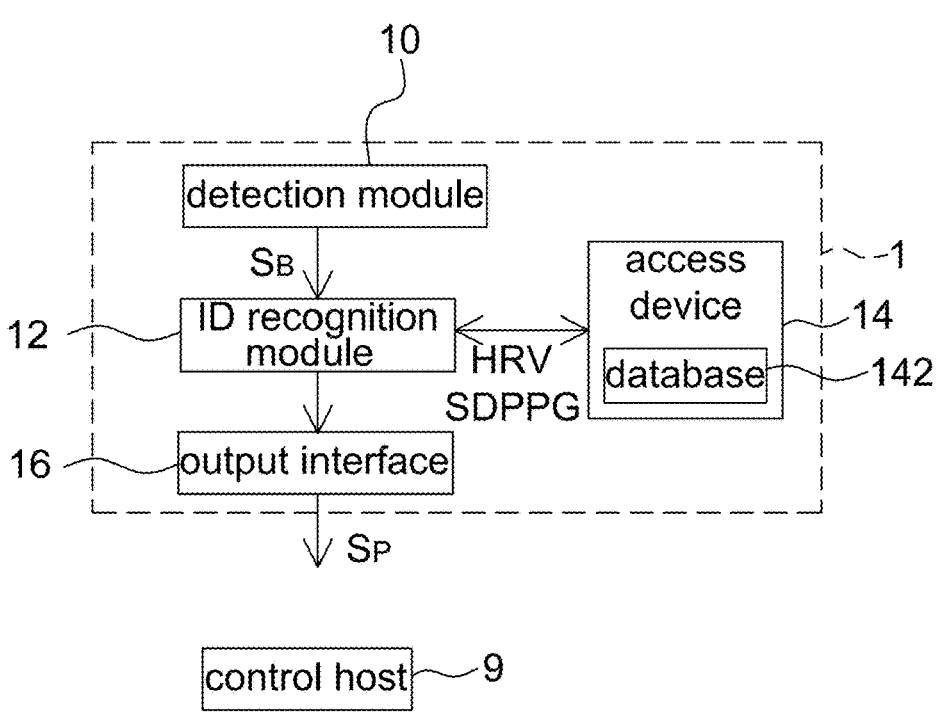
FIG. 1A is a block diagram of an individualized control system according to one embodiment of the present disclosure.

It should be noted that, wherever possible, the same reference numbers will be used throughout the drawings to refer to the same or like parts.

The present disclosure provides an individualized control system including a detection device and a control host. The detection device is adaptable to a wearable and/or portable accessory capable of being directly in contact with a human body skin, such as a watch, a bracelet, a foot ring, a necklace, eyeglasses, an earphone and a cell phone, but not limited thereto. The control host may include a microprocessor unit (MCU) or a central processing unit (CPU) or may be a computer system or a central control system. The control host controls, directly or via internet, the operation of a home appliance, a power system, a vehicle device, a security system, a warning device or the like, wired or wirelessly. The individualized control system of the present disclosure detects at least one biometric characteristic of a user through the detection device to be configured as a reference for ID recognition, and an ID signal is sent to the control host for individualized control, wherein said individualized control may be the automatic control according to the history record or the setting of the user, or the confirmation of the existence of the user so as to perform ON/OFF of a predetermined device.

In some embodiments, the biometric characteristic includes at least one of a blood oxygenation, a heart rate variability (HRV) and a second derivative of photoplethysmogram (SDPPG), wherein said biometric characteristic may be obtained by further processing PPG signals detected by the detection device, and said processing is known to the art and thus details thereof are not described herein. The inventors noticed that the heart rate variability and the second derivative of photoplethysmogram are different from person to person such that the heart rate variability and the second derivative of photoplethysmogram may be configured as a reference for ID recognition. In addition, the blood oxygenation changes with body conditions of a user, e.g. corresponding variation occurring at a fatigue state, and thus by continuously monitoring the blood oxygenation it is able to implement an interactive control with the user according to monitored results. The biometric characteristic further includes fingerprint and/or facial feature, and the technique of identifying an individual according to the detected fingerprint and facial feature is known to the art, and thus details thereof are not repeated herein.

In some embodiments, corresponding to the control system to which the control host is connected, said individualized control includes at least one of a home appliance control, a power system control, a vehicle device control, a security system control and a warning device control.

For example, when the control host receives the ID signal from the detection device, the control host may be used to control the setting, adjustment, output strength, directivity and ON/OFF of a home appliance so as to realize an intelligent control; for example, the ON/OFF or emission intensity of a light source at a specific region, the ON/OFF or operation strength of an air conditioner at a specific region, the channel selection of a television or an audio player, but not limited thereto.

For example, when the control host receives the ID signal from the detection device, the control host may be used to control the ON/OFF of a power system so as to realize an intelligent control; for example, the power supply at a specific region or of a specific equipment, but not limited thereto.

For example, when the control host receives the ID signal from the detection device, the control host may be used to control the setting, adjustment, output strength, directivity and ON/OFF of a vehicle device so as to realize an intelligent control; for example, the door lock operation, the strength and wind direction of an air conditioner, the position setting of a chair, the angle setting of a mirror, the channel setting of a radio, but not limited thereto.

For example, when the control host receives the ID signal from the detection device, the control host may be used to control the ON/OFF of a security system so as to realize a security control; for example, the setting of entrance control, the rise/fall of a gate, the ON/OFF of a monitoring system, but not limited thereto.

For example, when the control host receives the ID signal from the detection device, the control host may be used to control the ON/OFF of a warning system so as to realize an interactive control; for example, the prompting of history records, the fatigue warning, but not limited thereto. In this embodiment, after identifying a user according to the heart rate variability and second derivative of photoplethysmogram, the control host then accesses the record of blood oxygenation associated with the user and starts to monitor continuously. When a variation of the blood oxygenation being monitored indicates a fatigue state, a fatigue warning is provided, e.g. using audio, image, light, vibration or the like without particular limitations. It is appreciated that according to different ways of warning, the control host correspondingly controls the required device such as a speaker, a display device, a light source, a vibrator and so on.

Figure 1B:
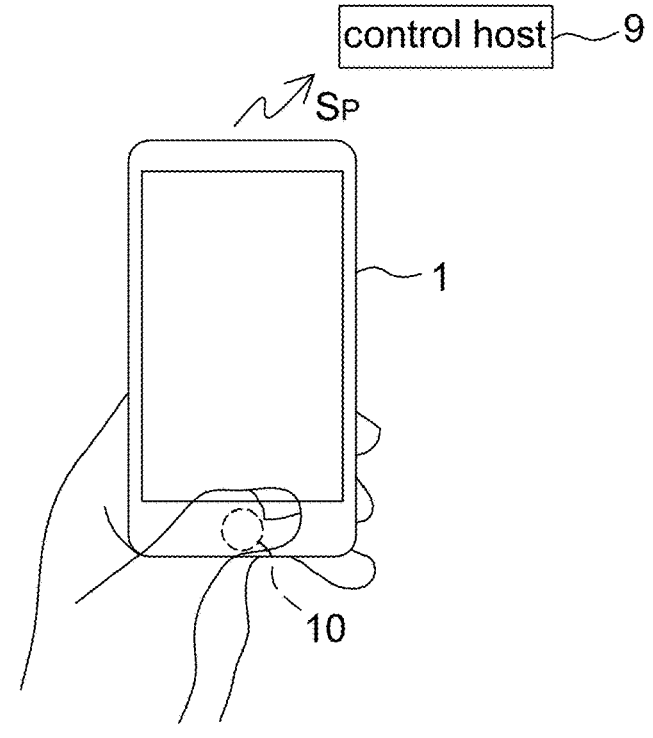
FIG. 1B is an operational schematic diagram of the individualized control system of FIG. 1A.

Referring to FIGS. 1A and 1B, FIG. 1A is a block diagram of an individualized control system according to one embodiment of the present disclosure and FIG. 1B is an operational schematic diagram corresponding to FIG. 1A, wherein a portable device, e.g. a cell phone, is shown as the detection device herein, but the present disclosure is not limited thereto.

The individualized control system of this embodiment includes a detection device 1 and a control host 9. The detection device 1 is configured to detect a biometric characteristic to identify a user identification (ID) according to the biometric characteristic, and output an ID signal according to the user ID. The control host 9 is configured to receive the ID signal to perform an individualized control, e.g. the above intelligent control, security control and/or interactive control, associated with the user ID according to the ID signal.

In this embodiment, the detection device 1 includes a biometric detection module 10, an ID recognition module 12, an access device 14 and an output interface 16. In one embodiment, the detection device 1 is configured to detect a biometric signal $S_B$ (i.e. PPG signals) from a skin surface to be sent to the ID recognition module 12. In another embodiment, the detection device 1 directly processes the biometric signal to generate a biometric characteristic, e.g. the above heart rate variability and/or second derivative of photoplethysmogram, to be sent to the ID recognition module 21.

The ID recognition module 21 then compares the biometric characteristic with pre-stored biometric characteristic information so as to identify a user ID. If the ID recognition module 21 receives the biometric signal $S_B$, the ID recognition module 21 firstly processes the biometric signal $S_B$ so as to generate the biometric characteristic and then performs the comparison so as to generate an ID signal $S_P$. If the ID recognition module 21 receives the biometric characteristic, the biometric characteristic is directly compared so as to generate the ID signal $S_P$.

The access device 14 stores the information of the blood oxygenation, heart rate variability and second derivative of photoplethysmogram associated with the user ID, wherein the information may be previously stored in a data construction procedure before operation (e.g. in a first startup) and updated according to new data detected during operation. The access device 14 may include a database 142 for storing the biometric characteristic information of one or a plurality of users. In addition, the access device 1 may access the biometric characteristic information associated with the user ID from an external database via internet; i.e. the database 142 may be at external of the access device 14.

The output interface 16 is preferably a wireless transmission interface, e.g. Bluetooth interface, microwave communication interface or the like, and is configured to output the ID signal $S_P$ to the control host 9. For example, the ID signal $S_P$ includes at least one ID bit configured to indicate ID information of the user, e.g. "1" indicating a valid ID and "0" indicating an invalid ID, but not limited thereto.

In this embodiment, the detection device 1 may be a portable device utilizing an optical detection method to detect the biometric characteristic (illustrated by examples below), wherein said optical method is referred to detecting PPG signals and obtaining the blood oxygenation, heart rate variability and/or second derivative of photoplethysmogram according to the PPG signals.

Figure 2A:
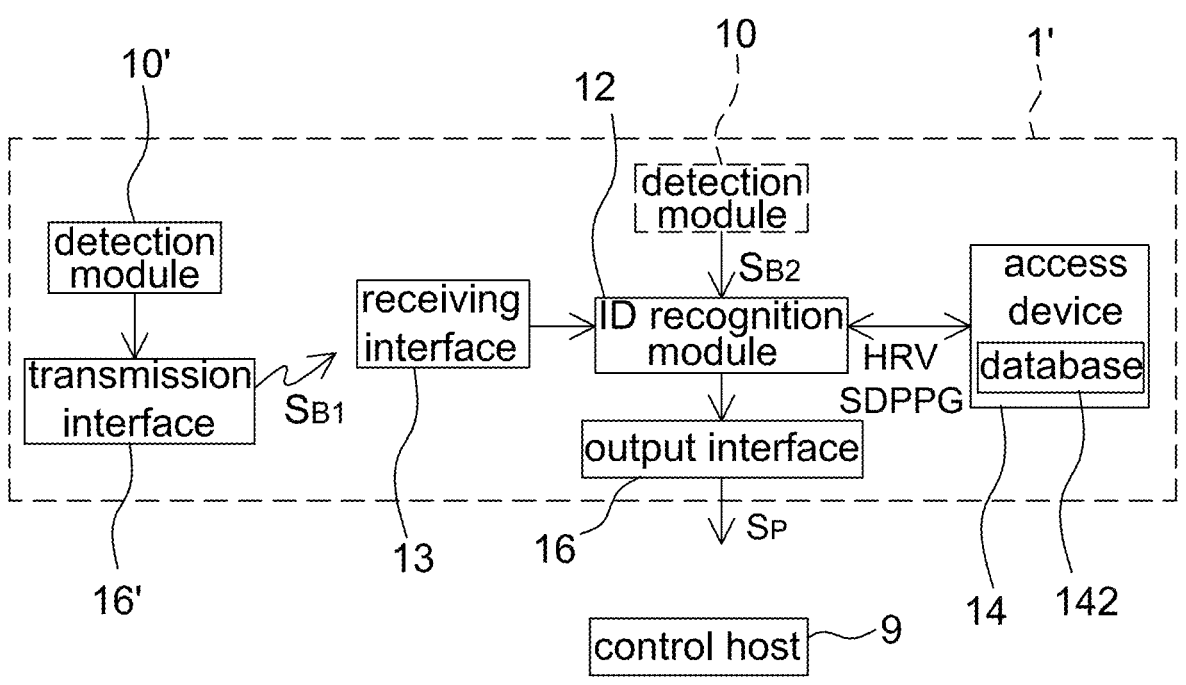
FIG. 2A is a block diagram of an individualized control system according to one embodiment of the present disclosure.
Figure 2B:
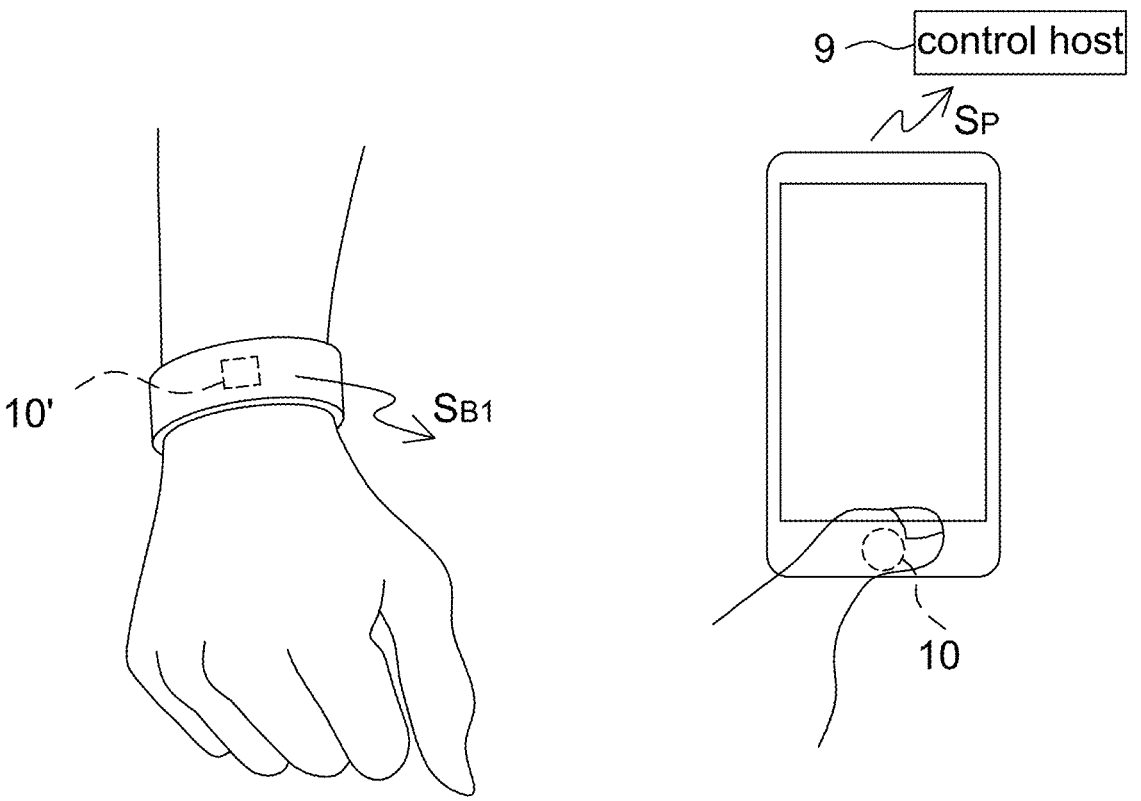
FIG. 2B is an operational schematic diagram of the individualized control system of FIG. 2A.

Referring to FIGS. 2A and 2B, FIG. 2A is a block diagram of an individualized control system according to another embodiment of the present disclosure and FIG. 2B is an operational schematic diagram corresponding to FIG. 2A, wherein the detection device 1' includes a portable device (e.g. shown as a cell phone herein) and a wearable accessory (shown as a bracelet herein), but the present disclosure is not limited thereto.

In one embodiment, the bracelet and the portable device detect the biometric characteristic using the optical detection method. For example, the bracelet includes a biometric detection module 10' and a transmission interface 16', wherein the biometric detection module 10' is configured to detect a first biometric signal $S_{B1}$, e.g. PPG signals. The transmission interface 16' sends the first biometric signal $S_{B1}$ to the portable device by wireless communication, e.g. Bluetooth communication. It is appreciated that the bracelet further includes a power module configured to provide the power required in operation. As mentioned above, the wearable accessory may be a watch, a foot ring, a necklace, eyeglasses or an earphone. In one embodiment, the bracelet may process the first biometric signal $S_{B1}$ at first so as to generate at least one biometric characteristic, and the transmission interface 16' transmits the biometric characteristic to the portable device wirelessly.

The portable device includes the ID recognition module 12, a receiving interface 13, the access device 14 and the output interface 16, wherein operations of the ID recognition module 12, the access device 14 and the output interface 16 are identical to those in the descriptions of FIG. 1A and thus details thereof are not repeated herein. After the receiving interface 13 receives the first biometric signal $S_{B1}$ from the transmission interface 16', the ID recognition module 12 generates a biometric characteristic according to the first biometric signal $S_{B1}$, compares the biometric characteristic with pre-stored biometric characteristic information to identify a user ID, and outputs an ID signal $S_P$ through the output interface 13 according to the user ID. As mentioned above, the biometric characteristic information may be previously stored in a database inside or outside of the access device 14. When the receiving interface 13 receives the biometric characteristic from the transmission interface 16', the ID recognition module 12 directly compares the received biometric characteristic with the pre-stored biometric characteristic information so as to identify a user ID.

In some embodiments, the portable device may include a detection module 10 configured to detect a second biometric signal $S_{B2}$, and the ID recognition module 12 identifies which of the first biometric signal $S_{B1}$ and the second biometric signal $S_{B2}$ is better, e.g. having a higher signal-to-noise ratio (SNR), and the better one is used in the following operation.

The control host 9 then performs an individualized control associated with the user ID according to the received ID signal $S_P$, wherein the individualized control has been described above and thus details thereof are not repeated herein.

In another embodiment, the bracelet and the portable device detect the biometric characteristic using an electrode detection method. For example, the bracelet and the portable device respectively have an electrode, and the bracelet is configured to detect a bio-electrical signal (e.g. the first biometric signal $S_{B1}$) from a left hand (or right hand) to be sent to the portable device. The portable device is configured to detect another bio-electrical signal (e.g. the second biometric signal $S_{B2}$) from the right hand (or left hand). The portable device (e.g. the ID recognition module 12) generates the heart rate variability (HRV) according to the first biometric signal $S_{B1}$ and the second biometric signal $S_{B2}$ to be configured as a reference data for ID recognition, wherein the principle of said electrode detection method is known to the art. As mentioned above, as the inventors noticed that the HRV is different from person to person, it may be adapted to the ID recognition. In addition, when the bracelet is replaced by a foot ring, a necklace, eyeglasses or an earphone, the detected positions are not limited to left and right hands.

Next, the operation of the optical biometric detection module 10 and 10' in the present embodiment is illustrated below, but the present disclosure is not limited thereto.

Figure 3A:
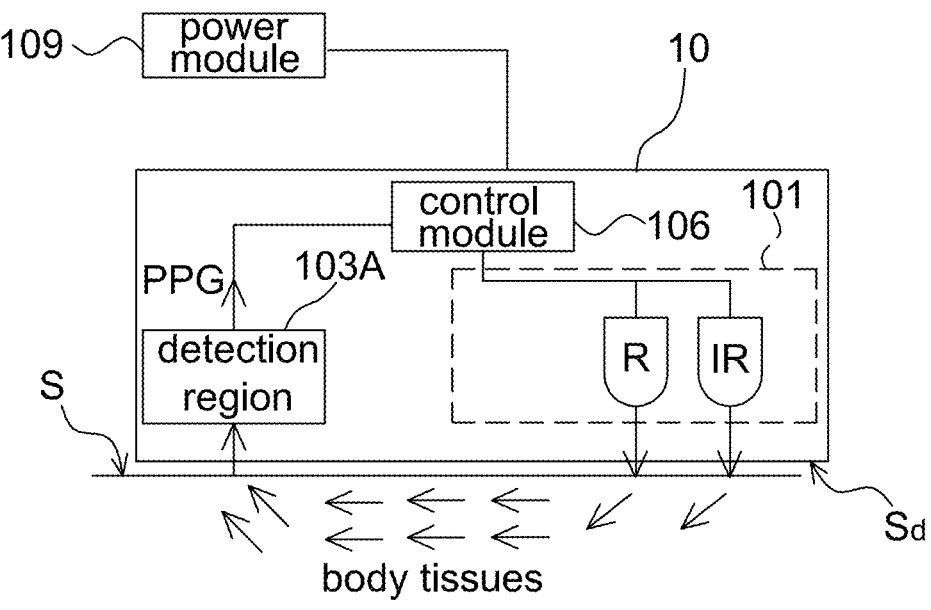
FIG. 3A is a block diagram of a biometric detection module according to one embodiment of the present disclosure.

Referring to FIG. 3A, it is a block diagram of a biometric detection module according to one embodiment of the present disclosure. The biometric detection module includes a light source module 101, a detection region 103A, a control module 106 and a power module 109. The detection module 10 is configured to detect at least one biometric characteristic, e.g. a heart rate variation, a blood oxygenation and/or a second derivative of photoplethysmogram, from a skin surface S via a detection surface Sd thereof, wherein the principle of detecting the heart rate variation, the blood oxygenation and the second derivative of photoplethysmogram according to PPG signals is known to the art and thus details thereof are not described herein. The power module 109 is configured to provide power required by the detection module 10 in operation. It should be mentioned that the power module 109 may directly use a power module of the portable device, i.e. the power module 109 may be outside of the detection module 10.

The light source module 101 includes, for example, at least one light emitting diode, at least one laser diode, at least one organic light emitting diode or other active light sources and is configured to emit red light and/or infrared light in a time division manner to illuminate the skin surface S, wherein the skin surface S is different according to different implementations of the detection device 1. In one embodiment, the light source module 101 includes a single light source whose emission spectrum is changeable by adjusting a driving parameter (such as the driving current or driving voltage) so as to emit red light and infrared light, wherein the red light and the infrared light are those generally used in the biometric detection. In another embodiment, the light source module 101 includes a red light source and an infrared light source configured to emit red light and infrared light, respectively. It is possible to use other light sources capable of emitting invisible light to illuminate the skin surface S as long as the biometric characteristic is detectable by analyzing the detected light signal. The invisible light does not bother the user during operation.

The detection region 103A is, for example, a semiconductor detection region which includes a plurality of detection pixels each including at least one photodiode configured to convert optical energy to electric signals. The detection region 103A is configured to detect penetrating light emitted from the light source module 101 for illuminating the skin surface S and passing through body tissues so as to correspondingly generate a red light signal and/or an infrared light signal, wherein the red light signal and the infrared light signal are photoplethysmographic signals or PPG signals. When the invisible light source is used, the detection region 103A generates corresponding light signals.

Figure 3B:
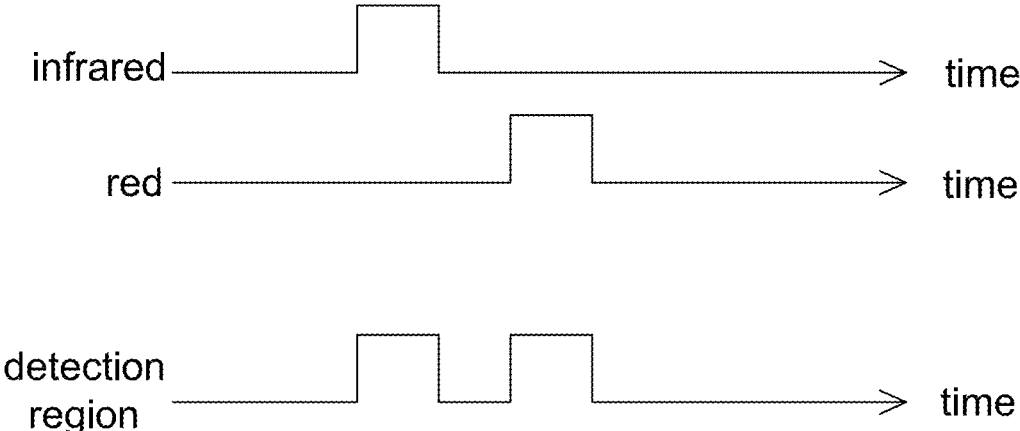
FIG. 3B is an operational schematic diagram of a biometric detection module according to one embodiment of the present disclosure.

The control module 106 is configured to control the light source module 101 to emit light in a time division manner and corresponding to the light detection of the detection region 103A, as shown in FIG. 3B, wherein the signal sequence shown in FIG. 3B is only intended to illustrate but not to limit the present disclosure. The control module 106 may directly calculate the biometric characteristic according to at least one of the red light signal and the infrared light signal, or may transmit the red light signal and the infrared light signal directly to the ID recognition module 12 to allow the ID recognition module 12 to calculate the biometric characteristic.

Figure 4:
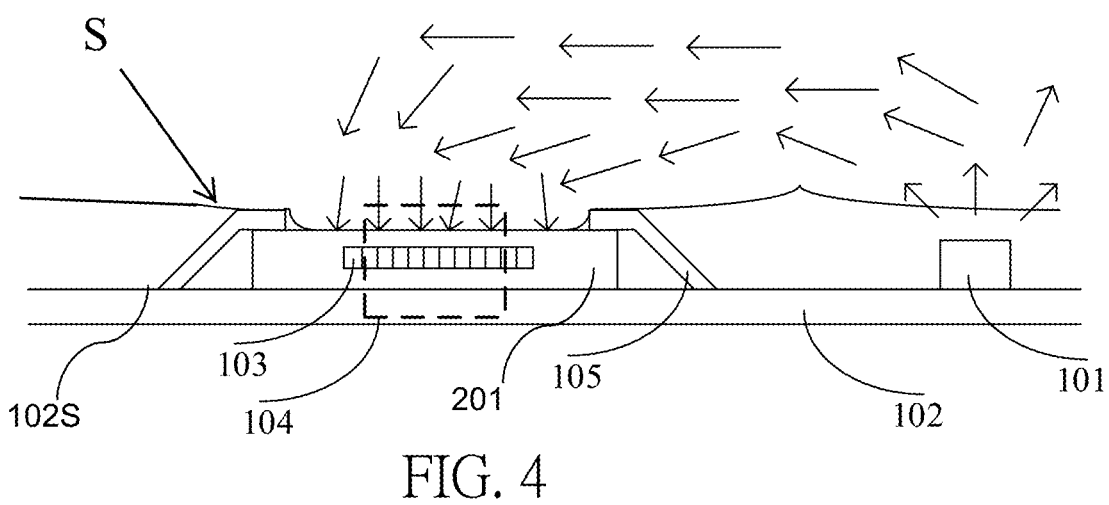
FIG. 4 is a schematic diagram of a thin biometric detection module according to one embodiment of the present disclosure.
Figure 7A:
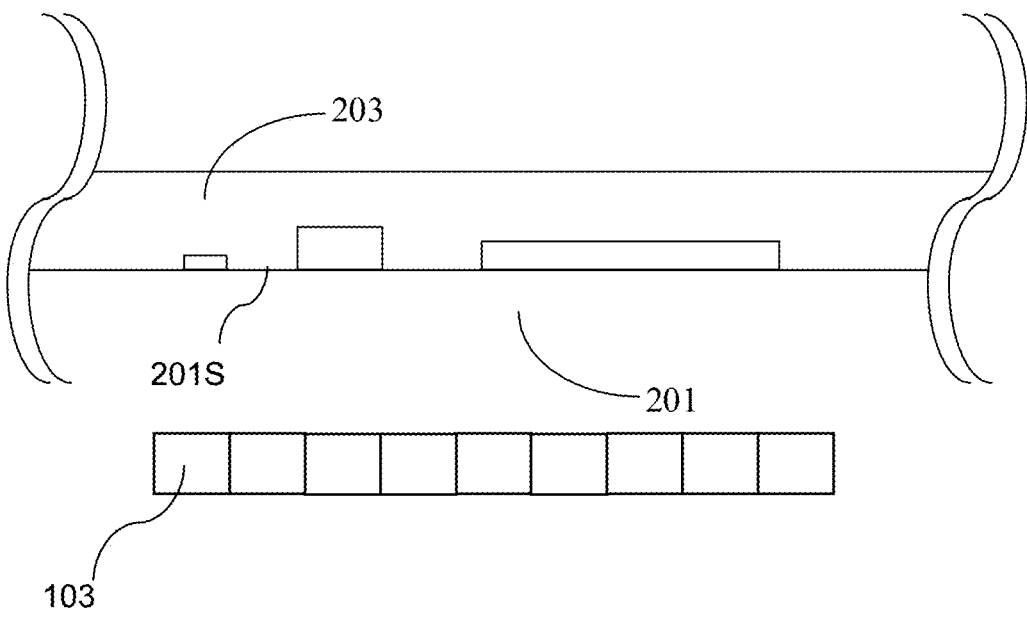
FIGS. 7A and 7B are cross-sectional views of the thin semiconductor structure of a biometric detection module according to some embodiments of the present disclosure.
Figure 7B:
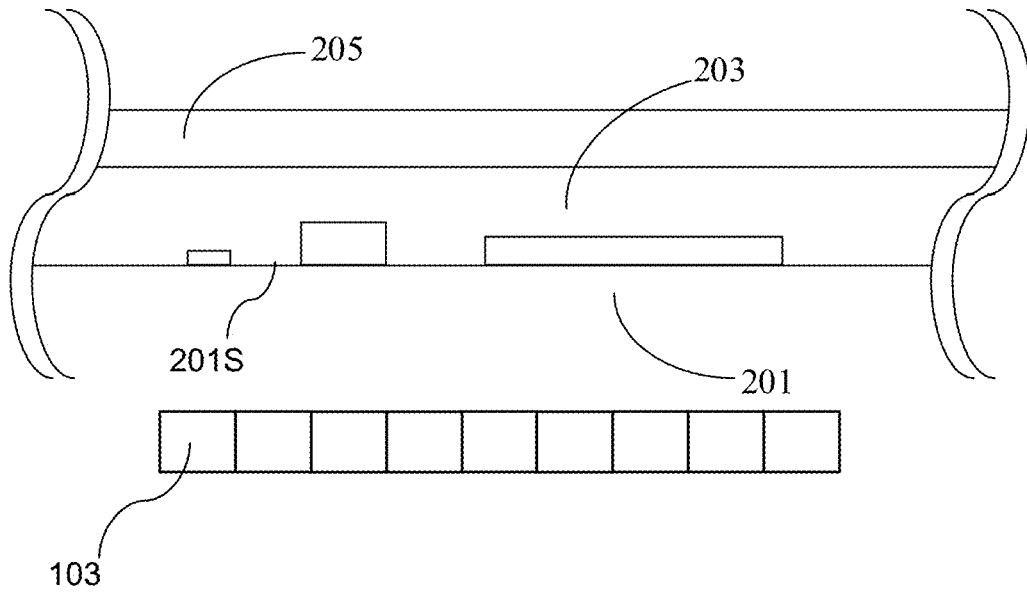

FIG. 4 shows a thin biometric detection module according to one embodiment of the present disclosure, which includes at least one light source module 101, a substrate 102, a plurality of detection pixels 103 and a plurality of contact points 105, wherein the detection pixels 103 form an optical semiconductor detection region 103A, which has a thin semiconductor structure 104 (further illustrated in FIGS. 7A and 7B). The contact points 105 are configured to electrically connect the optical semiconductor detection region 103A to the substrate 102 for being controlled by a control module 106 (as shown in FIG. 3A), wherein the detection pixels 103 may be arranged in a chip 201 and the contact points 105 are configured as outward electrical contacts of the chip 201. The light source module 101 is also electrically connected to the substrate 102, and the control module 106 is configured to control the light source module 101 to illuminate the skin surface S such that emitted light may enter the body tissues (e.g. the part of human body corresponding to the detection device) of a user. Meanwhile, the control module 106 is also configured to control the detection pixels 103 to detect light transmitting out from the body tissues. As vessels and blood in the body tissues have different optical properties, by arranging specific light source the biometric characteristic may be identified according to optical images detected by the detection pixels 103.

More specifically, the control module 106 may be integrated in the chip 201 or disposed on the substrate 102 (on the same or different surfaces of the substrate 102 with respect to the chip 201) and configured to control the light source module 101 and the optical semiconductor detection region 103A. The substrate 102 has a substrate surface 102S on which the chip 201 and the light source module 101 are disposed. In this embodiment, in order to effectively reduce the total size, a relative distance between the chip 201 and the light source module 101 is preferably smaller than 8 millimeters.

In some embodiments, the contact points 105 may be the lead frame structure. In other embodiments, the contact points 105 may be bumps, the ball grid array or wire leads, but not limited thereto.

In some embodiments, an area of the detection region 103A is larger than 25 mm$^2$. The optical semiconductor detection region may successively capture images at a frame rate higher than hundreds of frames per second. For example, the control module 106 may control the optical semiconductor detection region to capture optical images at a frame rate higher than 300 frames per second and control the light source module 101 to emit light corresponding to the image capturing.

Figure 5:
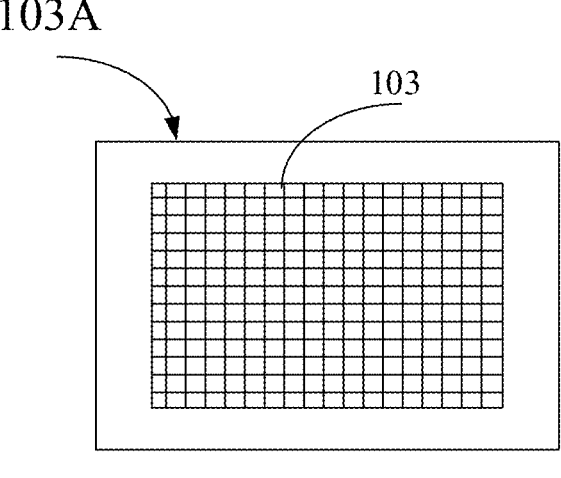
FIG. 5 is an upper view of the detection region of a biometric detection module according to one embodiment of the present disclosure.

FIG. 5 is an upper view of the optical semiconductor detection region 103A according to one embodiment of the present disclosure. In the application of detecting biometric characteristics, e.g. the blood oxygenation, the heart rate variation and the second derivative of photoplethysmogram, as the skin surface S does not have a fast relative movement with respect to the detection surface Sd, a size of the detection region 103A does not obviously affect the detected result. FIG. 5 shows the detection region 103A as a rectangular shape, and a ratio of the transverse and longitudinal widths may be between 0.5 and 2. Accordingly, no matter which of the biometric characteristics such as the vein texture, blood oxygenation, heart rate variation, blood pressure or second derivative of photoplethysmogram of a user is to be detected, the user only needs to attach the detection region 103A to the skin surface S. An area of the detection region 103A is at least larger than 25 mm$^2$.

Figure 6A:
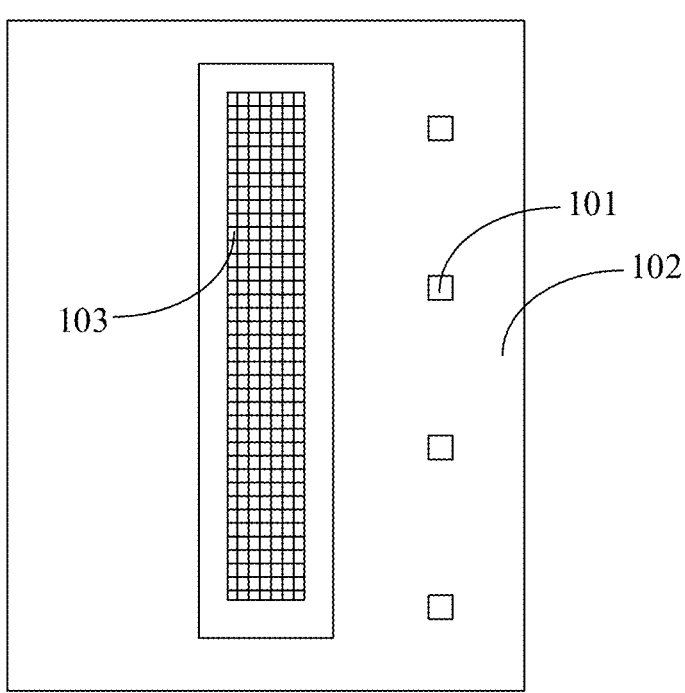
FIGS. 6A and 6B are upper views of a biometric detection module according to some embodiments of the present disclosure.
Figure 6B:
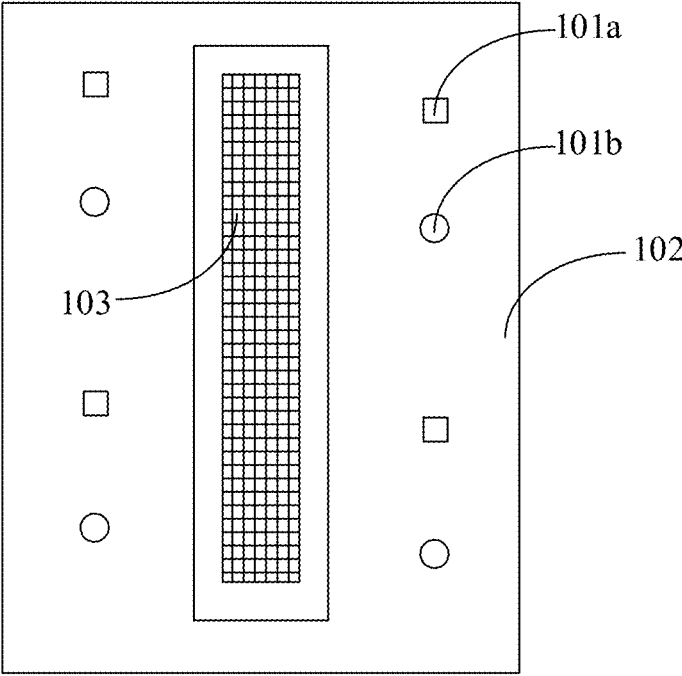

FIGS. 6A and 6B are upper views of a thin biometric detection module according to some embodiments of the present disclosure, which show the arrangement of light sources and the application using a plurality of light sources. In FIG. 6A, the light source module 101 is shown to be arranged at one side of a plurality of detection pixels 103 and electrically connected to the substrate 102. It should be noted that in this embodiment, although the light source module 101 is arranged at one side of the detection pixels 103, as the light may penetrate into the body tissues of the user, the position of the light source module does not affect a direction of the detection device as long as the skin surface is continuously illuminated by the light source module during the detection process.

In FIG. 6B, two different light sources 101a and 101b are shown. In this embodiment, the term "different light sources" is referred to the light sources emitting light of different wavelengths. As different components in the body tissues have different optical responses toward different light wavelengths, e.g. having different absorptions, by detecting different light sources the biometric characteristic associated with the light wavelengths may be derived and the correction may be performed according to the detected images associated with different light sources so as to obtain more correct detected results. For example, the oxygen component in the blood has different absorptions associated with different light colors, and thus by detecting the energy of different light colors the blood oxygenation may be derived. In other words, the thin biometric detection module according to some embodiments of the present disclosure may include two light sources 101a and 101b respectively emitting light of different wavelengths, e.g. red light and infrared light. And the optical semiconductor detection region may include two types of detection pixels configured to respectively detect different light wavelengths emitted from the light sources.

For example, if a blood oxygenation is to be detected, two light wavelengths close to the absorption wavelength 805 nm of HbO$_2$ and Hb may be selected, e.g. about 660 nm and 940 nm. Or the light wavelength between 730 nm and 810 nm or between 735 nm and 895 nm may be selected. The blood oxygenation may be derived according to the difference of light absorption of blood between the two light wavelengths, and the related detection technology is well known to the art and thus details thereof are not described herein.

According to FIGS. 6A and 6B, it is known that a plurality of light sources may be adopted in the present disclosure and is not limited to use only a single light source or two light sources. Furthermore, according to the biometric characteristic to be detected, different detection pixels may be arranged corresponding to more light sources, and positions of the light sources do not have particular limitations. In the thin structure, the biometric detection module of the present disclosure may be applied to detect various biometric characteristics. Different light sources may also be adopted in order to detect biometric characteristics. If it is desired to acquire uniform images, identical light sources may be arranged at both sides of same detection regions such that light may enter the body tissues from two sides of the same detection regions.

FIGS. 7A and 7B are cross-sectional views of the optical semiconductor detection region according to some embodiments of the present disclosure, which are partial schematic diagrams of the thin semiconductor structure 104. FIG. 7A is an embodiment in which a planar layer 203 also has the abrasion resistant ability. For example, the planar layer 203 made of polyimide material may have enough abrasion resistant ability to be adapted to the present disclosure. That is, the planar layer 203 is also configured as an abrasion resistant layer herein. The planar layer 203 is formed on the top of the chip structure 201 and on the chip surface 201S to overlay the optical semiconductor detection region for protecting the semiconductor structure 104. As the top of the chip structure 201 may have many convexes and concaves (as shown in the figure) after the metal layer and the electrode are formed thereon according to the semiconductor layout, the non-uniform surface has a negative effect to the optical detection and a weaker weather-proof ability. Accordingly, the planar layer 203 is formed on the top to allow the thin semiconductor structure 104 to have a flat surface to be suitable to the present disclosure. In the present disclosure, as the thin semiconductor structure 104 is exposed to air and directly in contact with the user's body frequently, a better abrasion resistant ability is required. In the semiconductor manufacturing technology nowadays, the polyimide-based material may be selected as the abrasion resistant material. Meanwhile, the planar layer 203 is preferably transparent to visible or invisible light corresponding to the selection of the light source. In addition, the abrasion resistant material may be glass material or the like. For example, the abrasion resistant layer is a glass layer.

It should be noted that in order to reduce the diffusion of light to blur the image when passing through the planar layer 203, preferably a distance from the surface of the semiconductor structure 104 to the surface of the chip structure 201, i.e. a thickness of the planar layer 203 herein, is limited to be smaller than 100 micrometers. That is, a distance from the chip surface 201S to an upper surface of the planar layer 203 (i.e. the abrasion resistant layer) is preferably smaller than 100 micrometers. When detecting the biometric characteristic, the upper surface of the planar layer 203 is configured as the detection surface Sd to be directly in contact with a skin surface S such that light emitted from the light source module 101 directly illuminates the skin surface S and sequentially passes through the body tissues and the planar layer 203 to be detected by the optical semiconductor detection region. In one embodiment, a distance between an emission surface of the light source module 101 and the substrate surface 102S is identical to a distance between upper surface of the planar surface 203 and the substrate surface 102S. That is, when the emission surface of the light source module 101 and the upper surface of the planar surface 203 have an identical height, the light emitted by the light source module 101 efficiently passes through the skin surface to enter the part of human body and is detected by the optical semiconductor detection region.

The difference between FIG. 7B and FIG. 7A is that the planar layer 203 in FIG. 7B does not have enough abrasion resistant ability, and thus another abrasion resistant layer 205 is formed upon the planar layer 203. Similarly, in order to reduce the diffusion of light when passing through the planar layer 203 and the abrasion resistant layer 205, in this embodiment a total thickness of the planar layer 203 and the abrasion resistant layer 205 is preferably limited to be smaller than 100 micrometers. In this embodiment, the planar layer 203 may be any material without considering the abrasion resistant ability thereof and the abrasion resistant layer 205 may be made of polyimide-based abrasion resistant material. In addition, the abrasion resistant material may be glass material or the like. For example, the abrasion resistant layer is a glass layer.

In some embodiments, it is possible to arrange a plurality of detection regions, e.g. arranging a plurality of linear detection regions along a predetermined direction or inserting a plurality of light sources between the linear detection regions. For example, the linear optical semiconductor detection regions may be arranged adjacent to each other, or the linear optical semiconductor detection regions and the light sources may be arranged alternatively so as to obtain a better optical imaging. As the detection principle is not changed, details thereof are not described herein.

Said substrate 102 is configured to electrically connect the light source module 101 and the detection pixels 103 and to allow the light source module to emit light to enter the body tissues, and the substrate may be a flexible soft substrate or a hard substrate made of hard material without particular limitations.

In the embodiment of a thin type structure, the optical semiconductor detection region may be directly attached to the skin surface of a user without other optical mechanism(s) to perform the image scaling and the light propagation. And thin and durable features thereof are suitable to be applied to wearable accessories.

In some embodiments, according to the adopted light source, different light filters may be formed during manufacturing the detection pixels to allow the desired light to pass through the filters and to be received by the detection pixels. The filters may be formed in conjunction with the semiconductor manufacturing process on the detection pixels using the conventional technology or formed on the detection pixels after the detection pixels are manufactured. In addition, by mixing filtering material in a protection layer and/or a planar layer, the protection layer and/or the planar layer may have the optical filter function. That is, in the embodiment of the present disclosure, said different detection pixels is referred to the detection pixels with different light filters but not referred to the detection pixels with different structures.

It is appreciated that in order to reduce the size, the biometric detection module 10 and 10' are illustrated by the embodiment shown in FIG. 4, but the present disclosure is not limited thereto. In some embodiments, other optical mechanism(s) may be disposed between the light source module 101 and the skin surface S to be detected and/or between the detection region 103A and the skin surface S to be detected according to different applications.

Figure 8:
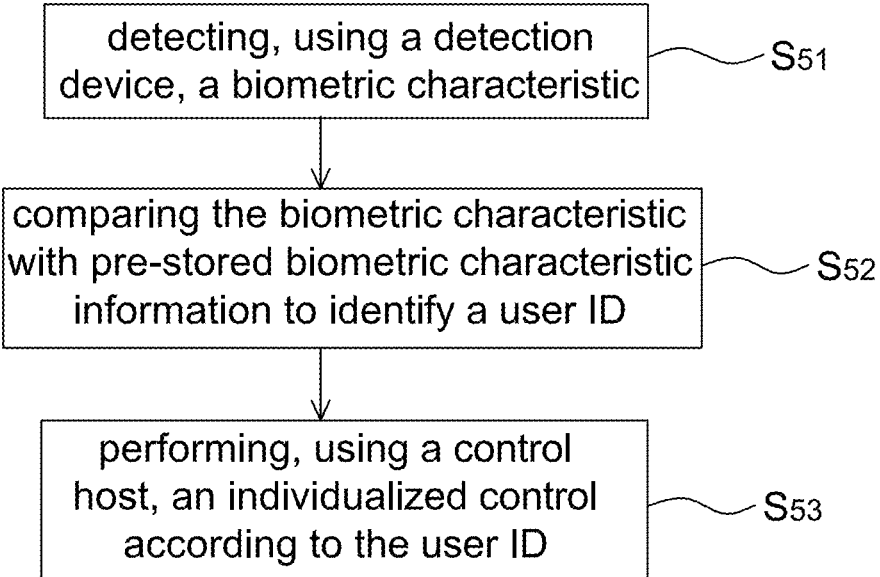
FIG. 8 is a flow chart of an operating method of an individualized control system according to one embodiment of the present disclosure.

Referring to FIG. 8, it is a flow chart of an operating method of an individualized control system according to one embodiment of the present disclosure, which includes the steps of: detecting, using a detection device, a biometric characteristic (Step $S_{51}$); comparing the biometric characteristic with pre-stored biometric characteristic information to identify a user ID (Step $S_{52}$); and performing, using a control host, an individualized control according to the user ID (Step $S_{53}$).

Steps $S_{51}$: If the detection device 1 is a portable device, the portable device directly detects the biometric characteristic and performs the ID recognition. If the detection device F includes a portable device and a wearable accessory (e.g. foot ring, bracelet, watch, necklace, eyeglasses or earphone), the operating method further includes the steps of: detecting, using the wearable accessory, a biometric signal (Step $S_{511}$); transmitting the biometric signal from the wearable accessory to the portable device (Step $S_{512}$); and generating, using the portable device, the biometric characteristic according to the biometric signal (Step $S_{513}$). In another embodiment, the wearable accessory may directly generate the biometric characteristic to be sent to the portable device, wherein the wearable accessory and the portable device are coupled to each other by Bluetooth communication.

Steps $S_{52}$: The portable device may directly compare the biometric characteristic with the pre-stored biometric characteristic information stored therein or compare the biometric characteristic with the biometric characteristic information pre-stored externally via internet. It is appreciated that the portable device has the function of connecting to the internet.

Step $S_{53}$: After the user ID is recognized, the portable device transmits, through wireless transmission, an ID signal $S_P$ to a control host so as to perform an individualized control, e.g. the above intelligent control, security control and/or interactive control.

In addition, the biometric characteristic information stored in the database may be automatically updated with the operation of the user so as to maintain the accuracy of the ID recognition.

The individualized control system of embodiments of the present disclosure is adaptable for electricity control of a large area, e.g., controlling the on/off and strength of illumination lights, the on/off and strength of air conditioners and/or the on/off of monitoring cameras in partial area(s) of the whole large area according to the identified user ID to fulfill the requirements of the energy conservation and carbon reduction.

For example, in a smart parking lot including a plurality of illumination lights and monitoring cameras, the illumination lights and monitoring cameras are arranged corresponding to a plurality of parking spaces and passways, e.g., at least one illumination light arranged corresponding to one parking space, and one illumination light arranged every a predetermined distance at the passway going to the one parking space. The control host 9 of the individualized control system controls the operation of a entrance gate of the smart parking lot, the operation of illumination lights and monitoring cameras in an area of a specific parking space associated with a specific user (i.e. the identified user ID), the operation of illumination lights and monitoring cameras in an area of a specific passway to the specific parking space, e.g., the passway from the entrance gate to the specific parking space and from the specific parking space to an elevator entrance.

The control host 9 is arranged, for example, near the entrance gate and/or the elevator entrance of the smart parking lot for receiving ID signal Sp from the detection device 1, 1' when the detection device 1, 1' enters a detecting range of the control host 9. Accordingly, when the detection device 1, 1' identifies, e.g., according to characteristic coding, the biometric characteristic of a current user belonging to a specific user (e.g., by comparing with pre-stored characteristic coding in the database 142), the ID signal Sp associated with the specific user is then wired or wirelessly sent to the control host 9. After receiving the ID signal Sp, the control host 9 opens the entrance gate, turns on the illumination light(s) and monitoring camera(s) in an area of a specific parking space associated with the specific user, turns on the illumination light(s) and monitoring camera(s) in an area of a passway to the specific parking space, and keeps the illumination lights and monitoring cameras in the rest areas being turned off such that most of illumination lights and monitoring cameras in the smart parking lot are turned off and only those arranged in areas to be used by the specific user are turned on to effectively save power and improve the control performance.

As mentioned above, the detection device 1, 1' has database 142 which previously stores information of a specific parking space and a passway to the specific parking space respectively associated with each of a plurality of system user IDs. For example, a first user ID is previously recorded to use a first parking space and a first specific passway to the first parking space; a second user ID is previously recorded to use a second parking space and a second specific passway to the second parking space; and so on. In one embodiment, the ID signal Sp includes multiple bits to indicate information of the specific parking space and the specific passway to the specific parking space.

In other embodiments, the database 142 is included in the control host 9. The detection device 1, 1' recognizes a current user ID and sends an ID signal Sp associated with the current user ID to the control host 9. The control host 9 then reads control information of the illumination lights, air conditioners and cameras from the database 142 therein according to the received ID signal Sp.

As illustrated in one embodiment above, the detection device is composed of a wearable accessory (e.g., a bracelet) and a portable device (e.g., a cell phone). The wearable accessory is used to detect light signals (e.g., red light signal and infrared light signal). The portable device wirelessly receives raw data of the light signals from the wearable accessory and generates PPG signals, time-domain signals and/or frequency-domain signals of SDPPG (referring to FIGS. 9 and 10). The portable device compares current time-domain signals and/or frequency-domain signals of SDPPG (associated with a current user) with pre-stored characteristic coding of SDPPG to perform the ID recognition. Once a user ID is identified to be one of a plurality of users recorded in the database 142, the corresponding control associated with the identified user ID is executed by the control host 9.

Nowadays, SDPPG is often used for indicating the arterial stiffness, but is not used as a tool for recognizing a user ID. The SDPPG is obtained by performing a second derivative on the PPG signal (e.g., the red and/or infrared PPG signal) detected by the detection device 1, 1'. Corresponding to different users, characteristic parameters or vectors of the SDPPG are respectively coded as characteristic coding to be stored in the database 142 previously, wherein the characteristic parameters or vectors include, for example, characteristic values of time-domain signals and/or frequency-domain signals of the SDPPG.

Figure 9:
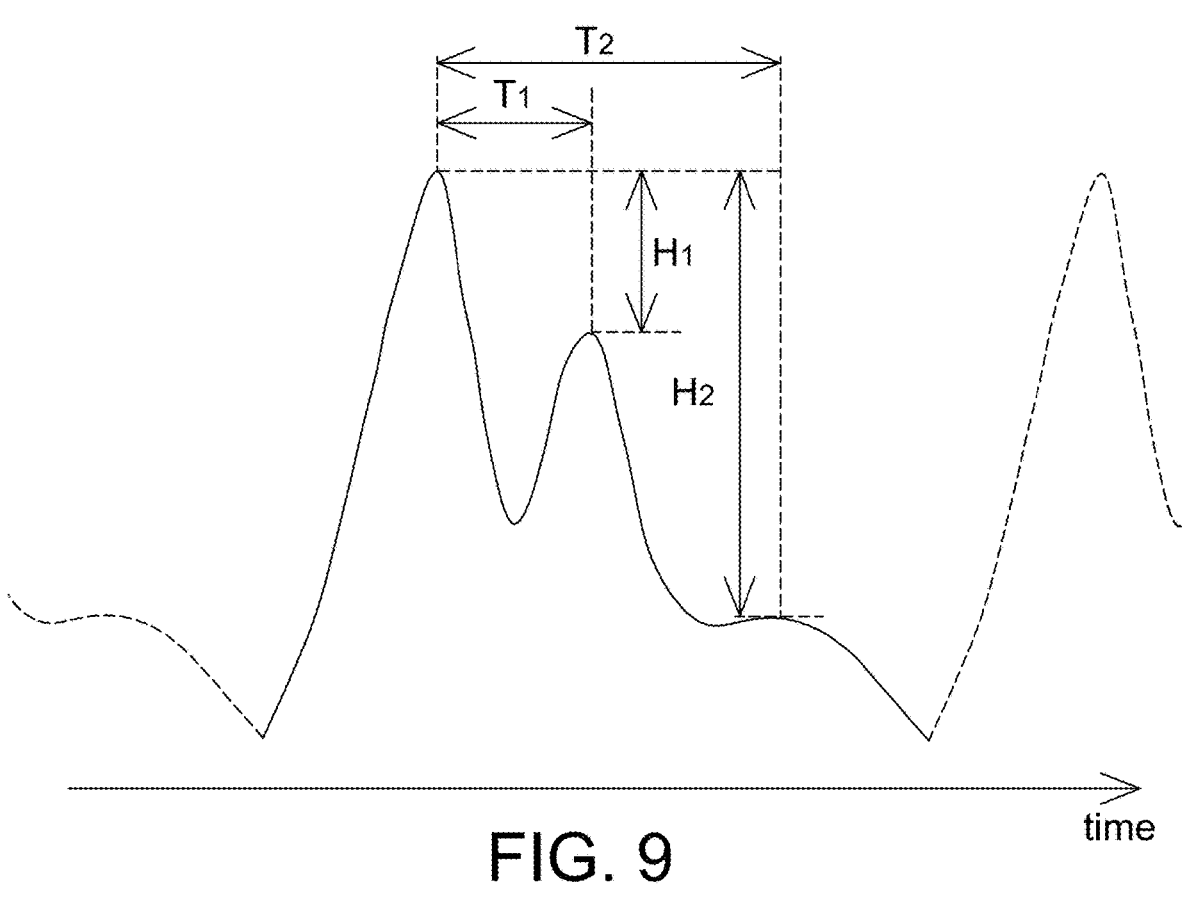
FIG. 9 is a schematic diagram of time-domain SDPPG signal obtained according to a PPG signal detected by a detection device according to one embodiment of the present disclosure.
Figure 10:
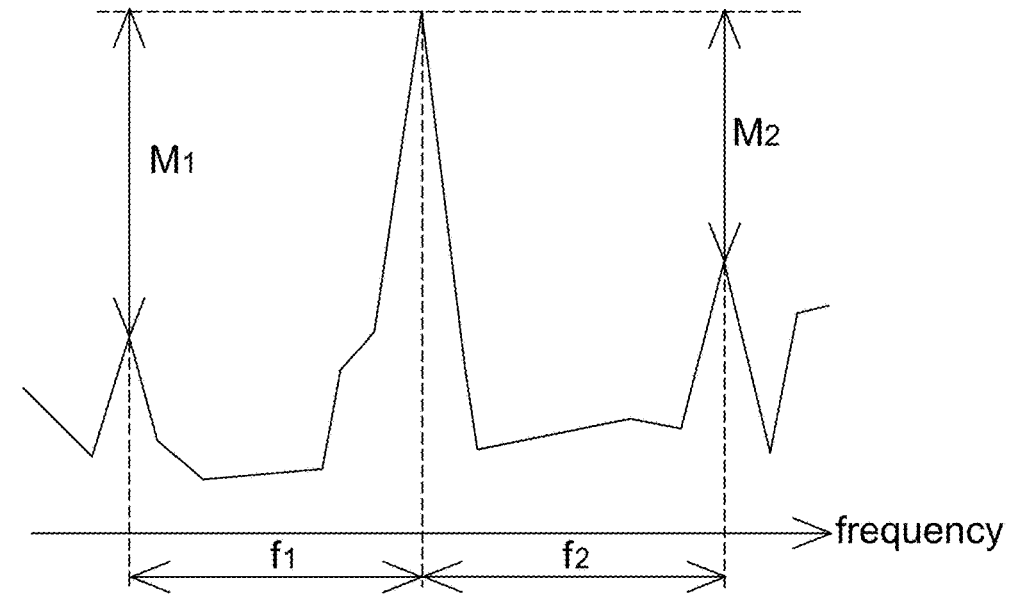
FIG. 10 is a schematic diagram of frequency-domain SDPPG signal obtained according to a PPG signal detected by a detection device according to one embodiment of the present disclosure.

Referring to FIGS. 9 and 10, FIG. 9 is a schematic diagram of time-domain SDPPG signal obtained according to a PPG signal detected by a detection device according to one embodiment of the present disclosure, and FIG. 10 is a schematic diagram of frequency-domain SDPPG signal obtained according to a PPG signal detected by a detection device according to one embodiment of the present disclosure. The PPG signal detected by the detection device 1, 1' is an oscillating signal in time domain, and thus the SDPPG obtained thereby also oscillates with time as shown in FIG. 9. It is appreciated that if the detection device 1, 1' performs the ID recognition according to the frequency-domain signal of SDPPG, the detection device 1, 1' further includes a frequency conversion unit for converting the time-domain signal in FIG. 9 to the frequency-domain signal in FIG. 10. The frequency conversion unit is implemented by software, hardware or a combination thereof. As mentioned above, corresponding to different users (or user IDs), the detection device 1, 1' obtains different time-domain signals and frequency-domain signals of SDPPG. This difference is coded and used as a way to distinguish different users in the present disclosure.

In the data construction procedure before operation, the detection device 1, 1' is operated to take at least one distance (i.e. time difference) as well as magnitude difference or ratio between time-domain signal peaks of SDPPG as characteristics to be coded, e.g., taking (H1, H2, T1, T2) or (H2/H1, T1, T2) as characteristic coding, and store one characteristic coding corresponding to each of multiple system users, wherein H1, H2, T1, T2, H2/H1 are digital codes with 2 bits, 4 bits or more bits. In operation, when the detection device 1, 1' detects the time-domain signal of SDPPG of a current user (e.g., shown in FIG. 9), the characteristic coding of SDPPG of the current user is generated and compared with the pre-stored characteristic coding associated with a plurality of users to perform the ID recognition. More specifically, the characteristic coding of SDPPG includes at least one time difference (e.g., T1, T2) and at least one amplitude difference (e.g., H1, H2) between time-domain signal peaks of SDPPG. In this embodiment, one of the time-domain signal peaks is a maximum peak within one of repeatedly successive second derivative of photoplethysmograms calculated by the detection device 1, 1', e.g., the first peak shown to have a maximum value in FIG. 9. It is appreciated that the pre-stored characteristic coding in the database 142 may be automatically updated each time the associated user ID is identified.

To increase the identification accuracy, in the data construction procedure the detection device 1, 1' further takes at least one distance (i.e. frequency difference) as well as intensity difference or ratio between frequency-domain signal peaks of SDPPG as characteristics to be coded, e.g., taking (M1, M2, f1, f2) or (M2/M1, f1, f2) as characteristic coding, and stores one characteristic coding corresponding to each of multiple system users, wherein M1, M2, f1, f2, M1/M2 are digital codes with 2 bits, 4 bits or more bits. More specifically, the characteristic coding further includes at least one frequency difference (e.g., f1, f2) and at least one intensity difference (e.g., M1, M2) between frequency-domain signal peaks of SDPPG, wherein one of the frequency-domain peaks has a maximum intensity value. In other embodiments, the detection device 1, 1' performs the ID recognition only according to the frequency characteristic coding without according to the time characteristic coding.

In addition, the conventional machine learning or rule based method may be used to perform the characteristic learning and categorizing on the time-domain and/or frequency-domain signals of SDPPG to identify characteristic parameters or vectors corresponding to different users. Accordingly, when the current PPG signal of a current user is detected by the detection device 1, 1', the detection device 1, 1' performs the characteristic analyzing on SDPPG obtained from the detected current PPG signal and compares the analyzed result with pre-stored characteristic parameters or vectors (e.g., characteristic coding) in the database 142 to recognize the user ID of the current user. Corresponding control is then executed.

It is appreciated that a number and values of characteristic values in FIGS. 9 and 10 are only intended to illustrate but not to limit the present disclosure.

In another embodiment, in addition to controlling the illumination lights at a specific parking space and passway associated with the identified user ID, the individualized control system of the present disclosure is further used to perform the vehicle autopilot in the smart parking lot after a vehicle entering the gate.

Figure 11:
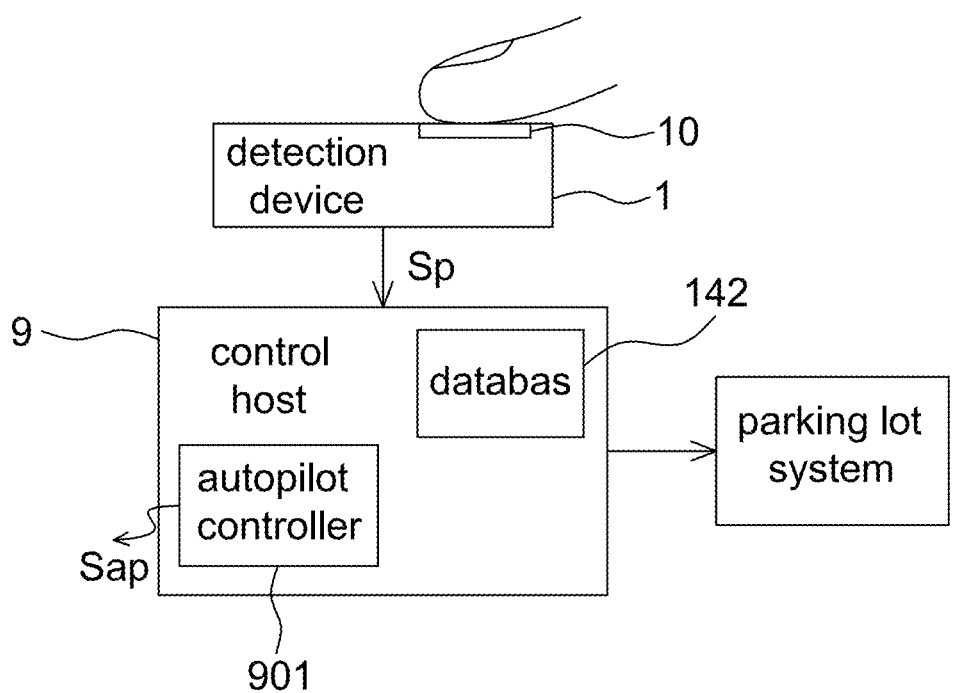
FIG. 11 is a block diagram of an individualized control system adapted to a smart parking lot according to another embodiment of the present disclosure.

Referring to FIG. 11, it is a block diagram of an individualized control system adapted to a smart parking lot according to another embodiment of the present disclosure. The individualized control system herein also includes a detection device 1 and a control host 9 as FIGS. 1A and 2A. The detection device 1 and the control host 9 perform identical operations mentioned above, e.g., controlling the parking lot system including lights, cameras and/or gates. Furthermore, the control host 9 in this embodiment has an autopilot controller 901 used to automatically guide a car to a specific parking space, which is determined according to the ID signal Sp received from the detection device 1, through the associated passway. The autopilot controller 901 is integrated in a CPU, MCU or ASIC of the control host 9.

In this embodiment, the database 142 is shown to be included in the control host 9, but not limited to. The database 142 also previously stores information of a specific parking space and a passway to the specific parking space respectively associated with each of a plurality of user IDs. When a current user ID, which is associated with the ID signal Sp from the detection device 1, matches a predetermined user ID previously stored in the database 142, the autopilot controller 901 of the control host 9 automatically guides, e.g., by wirelessly sending an autopilot signal Sap, a car to the specific parking space associated with the specific user ID according to the received ID signal Sp. The autopilot signal Sap includes information of moving speed and moving direction.

Figure 12:
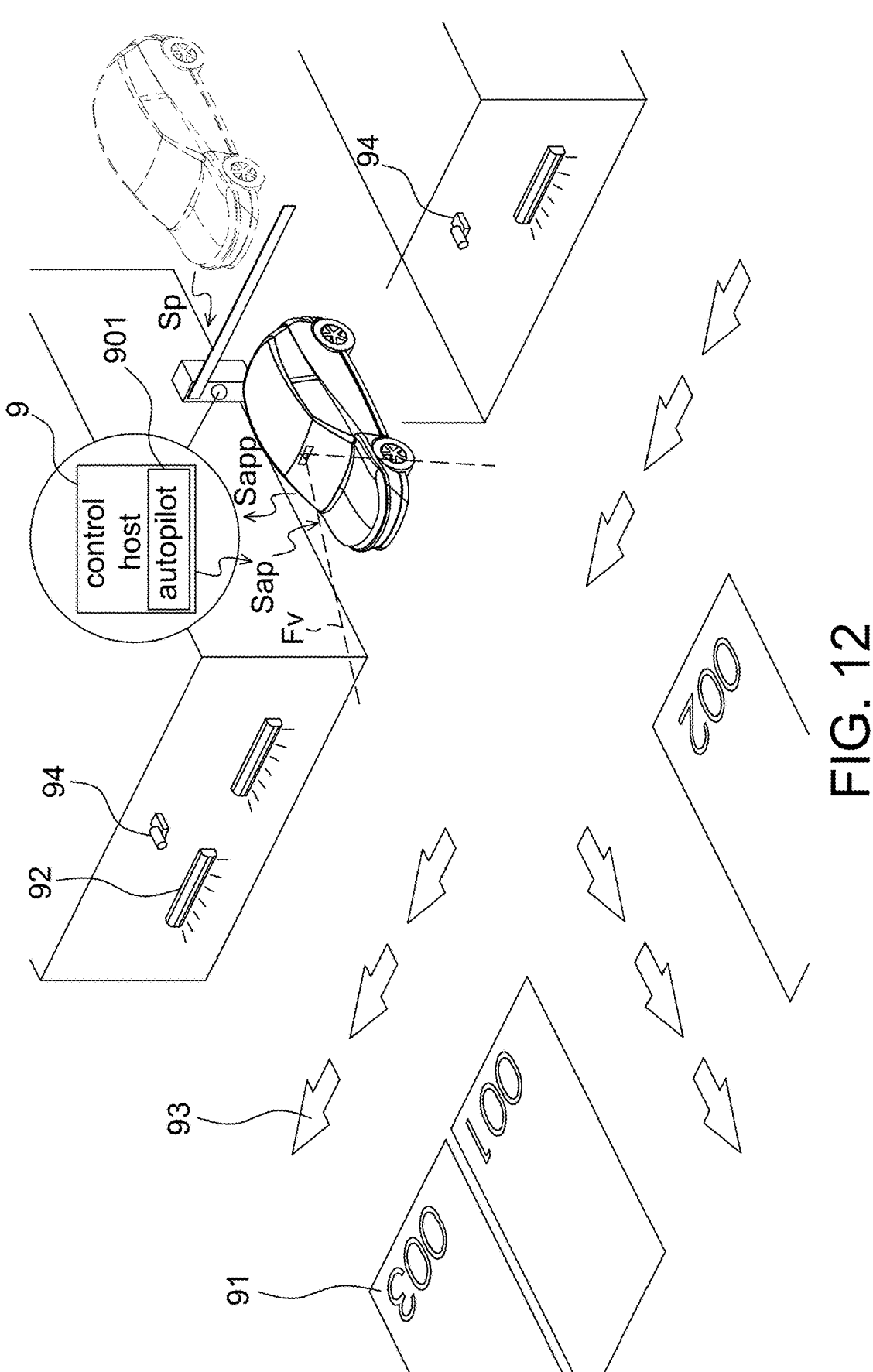
FIG. 12 is a schematic diagram of a smart parking lot according to an embodiment of the present disclosure.

It is appreciated that, in this embodiment, the car to be guided by the autopilot controller 901 has an autopilot mode. Referring to FIG. 12, it is a schematic diagram of a smart parking lot according to an embodiment of the present disclosure. For example, the specific user sitting in the car pushes a button or selects to enter the autopilot mode, and the car transmits an autopilot permission signal Sapp to the control host 9 to construct a wirelessly communication between the car and the control host 9. Then, the control host 9 starts to send the autopilot signal Sap to automatically guide the car after receiving the autopilot permission signal Sapp from the car.

The vehicle autopilot is implemented by suitable ways. For example, the control host 9 analyzes pictures captured by multiple cameras, e.g., 94, or signals detected by RFID tags in the smart parking lot to determine a current position of the car, and the control host 9 sends commands (e.g., autopilot signal Sap), which contains a moving speed, a moving direction, a target parking space and the associated passway, to the car to lead the car to the target parking space. The control host 9 automatically monitors the movement of all cars in the smart parking lot by the cameras 94 or the RFID tags. The arrangement of the RFID tags is known to the art and thus details thereof are not described herein.

In another example, the smart parking lot further comprises a plurality of directing lights 93 arranged on the floor and/or walls. The control host 9 analyzes pictures captured by multiple cameras, e.g., 94, or signals detected by RFID tags in the smart parking lot to determine a current position of the car, and the control host 9 sequentially turns on the directing lights 93 in the passway to guide the car to the target parking space. In this example, the car is arranged with at least one camera each having a field of view FV for taking pictures around the car. The car has a processing unit such as a CPU, MCU or ASIC in the vehicle central control to analyze the captured pictures, e.g., identifying images of the directing lights 93 in the pictures to determine the moving direction and moving speed, such that the car is navigated to the target parking space by following the lighted directing lights 93 in the passway.

It is possible to use other autopilot methods to automatically guide the car to the specific parking space as long as the car has a function to communicate with the control host 9 to allow the control host 9 to direct the car in a suitable way to the specific parking space which is confirmed by accessing the database 142 according to the ID signal sent from the detection device 1.

In the above embodiments, the ID signal Sp is associated with a user and identified according to the biometric characteristic of the user. In an alternative embodiment, the ID signal Sp is associated with a device instead of a user, i.e. the ID signal Sp indicating a device ID. This embodiment is for a scenario that one car is used by several people but using the same portable electronic device. Of course, it is possible that said several people have different portable electronic devices only said different portable electronic devices all being registered in the individualized control system previously. For example, each portable electronic device is registered in the individualized control system using Bluetooth linkage and the device ID is recorded in the database 142 previously.

Accordingly, in this embodiment, the portable electronic device is used to wirelessly send an ID signal Sp associated with the portable electronic device, which has been previously recorded in the database 142 of the individualized control system. For example, when the communication is implemented by wireless technique, a linkage is automatically or manually setup when the car enters a link range. Similarly, the database 142 in this embodiment previously stores information of a specific parking space and a passway to the specific parking space respectively associated with each of a plurality of device IDs. The host controller 9 wirelessly receives the ID signal Sp from the portable electronic device, accesses the database 142 to identify a current device ID associated with the received ID signal Sp; and turns on the illumination lights in areas of the specific parking space and the passway associated with the current device ID according to the received ID signal Sp. It is appreciated that when the current device ID is not found in the database 142, the gate of the smart parking lot is not opened by the control host 9, and the control host 9 does not perform any corresponding control of the parking lot system.

The host controller 9 in this embodiment performs similar operations as the above embodiments only the ID signal to be identified and compared being related to the device in this embodiment. For example, the control host 9 is further used to automatically guide a car to the specific parking space associated with the identified device ID. In this case, even if the portable electronic device in the car is used by different persons, the car is still led to the parking space associated with the device ID by the control host 9.

It is appreciated that the portable electronic device may confirm whether a current user is a legal user before entering the operation system of the portable electronic device. For example, the current user is asked to enter a password or a predetermined gesture to enter the operation system of the portable electronic device, and the ID signal is sent when a match of the password or the predetermined gesture is confirmed, e.g., when starting to drive the car or just before passing the gate, by the portable electronic device. The method of checking a password or a predetermined gesture by a portable electronic device is known to the art, e.g., the password or the predetermined gesture is set by the legal user previously in a security setting. In another embodiment, it is possible that the portable electronic device includes the above detection device 1 to detect a biometric characteristic of a user, and the ID signal is sent when a match of the biometric characteristic is confirmed, e.g., when starting to drive the car or just before passing the gate, by the portable electronic device. That is, the host controller 9 does not confirm the user but confirms the registered devices. It is the portable electronic device to perform the confirming of the legal operator.

Figures 13A, 13B:
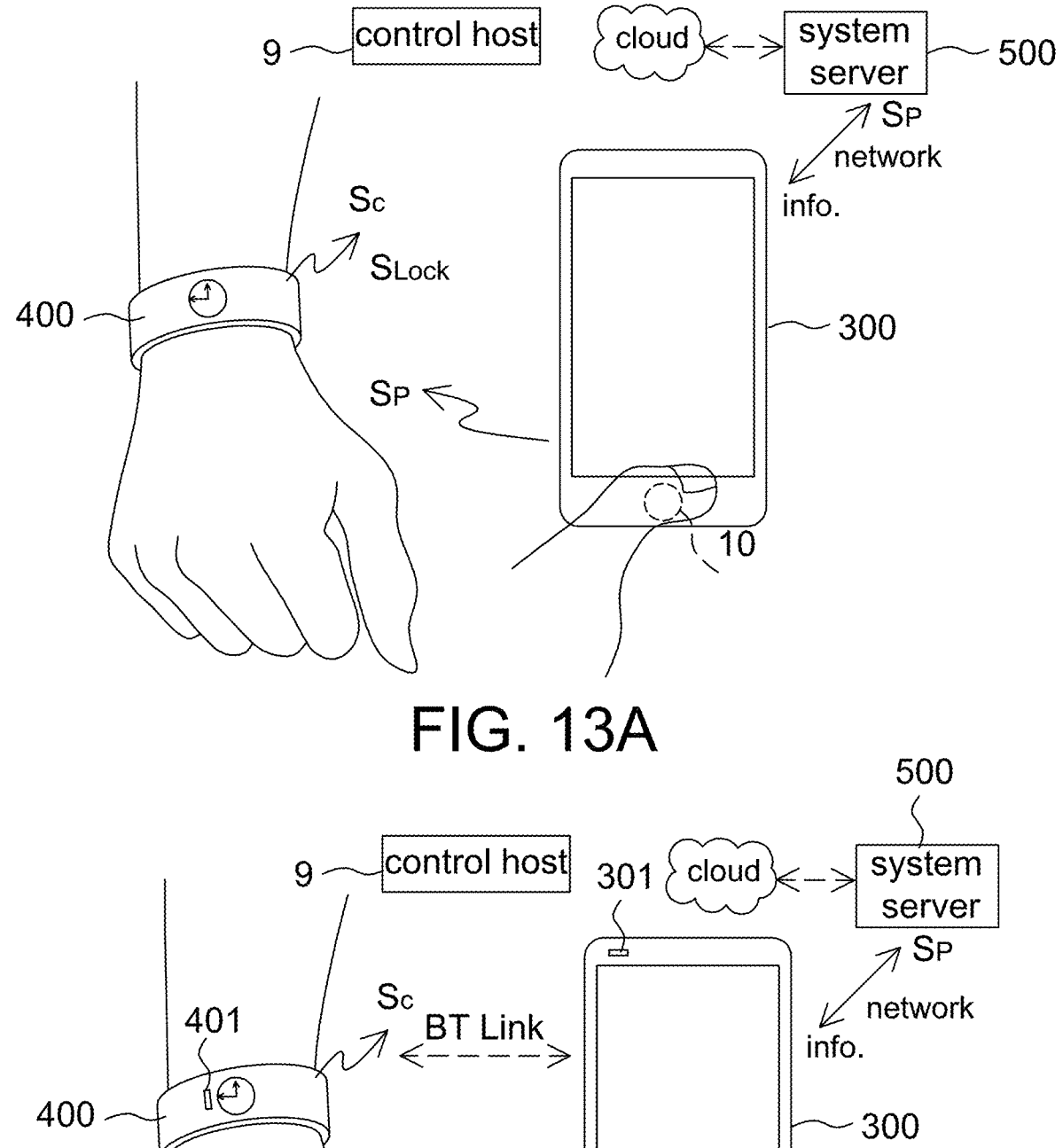
FIGS. 13A and 13B are operational schematic diagrams of an individualized control system according to some embodiments of the present disclosure.

Referring to FIG. 13A, it is a schematic diagram of an individualized control system according to another embodiment of the present disclosure. The individualized control system includes a portable device 300, a wearable accessary

400 and a control host 9, wherein the type of and the executed individualized control by the control host 9 have been illustrated above, and thus details thereof are not repeated herein.

In FIG. 13A, a watch is shown to represent the wearable accessary 400, and a smartphone is shown to represent the portable device 300, but the present disclosure is not limited thereto. The portable device 300 is further selected from a tablet computer, a personal digital assistance (PDA), a notebook computer or the like. The wearable accessary 400 is a bracelet, a watch, a foot ring, a necklace, eyeglasses, an earphone or the like as long as it can be worn by a user.

In this embodiment, the portable device 300 is used to detect a biometric characteristic to identify a user ID according to the biometric characteristic. The portable device 300 further outputs an ID signal Sp according to the identified user ID. As mentioned above, the biometric characteristic includes a heart rate variability (HRV) and a second derivative of photoplethysmogram (SDPPG), e.g., obtained from the detected PPG signal which is detected by the detection module 10. Details of detecting the HRV and SDPPG and generating the ID signal Sp have been described above, and thus details thereof are not repeated herein.

In this embodiment, the biometric characteristic is not limited to the HRV and SDPPG. In other embodiments, the biometric characteristic is a fingerprint, an iris, a face, a voiceprint or an atrial fibrillation (AF) that indicates an individual character of a user. It is appreciated that when the fingerprint is used as the biometric characteristic, the portable device 300 further includes a fingerprint detector, which is an optical type or an electrode type without particular limitations. When the iris or face is used as the biometric characteristic, the portable device 300 further includes an image sensor used to capture an iris image or a face image. When the voiceprint is used as the biometric characteristic, the portable device 300 further includes a microphone to collect the user's speech. When the AF is used as the biometric characteristic, the portable device 300 further includes the detection module 100 to detect the PPG signal or includes electrodes to detect ECG. The portable device 300 includes a processor such a MCU or CPU for performing the ID recognition according to the detected signals, e.g., audio signals, image signals, ECG signals, PPG signals.

The wearable accessary 400 is used to detect a heartbeat, e.g., including the detection module 10' (as shown in FIG. 2B) on a side thereof facing the user's skin to detect a PPG signal, and calculate the heartbeat using the PPG signal in a time domain or a frequency domain. When receiving the ID signal Sp and continuously detecting the heartbeat, the wearable accessary 400 sends a confirmed signal Sc to the control host 9; whereas, when the heartbeat is not detected, the confirmed signal Sc is not sent. In some embodiments, the heartbeat is identified not detectable when the signal-to-noise (SNR) of the PPG signal in time domain is too low or the main frequency of the heartbeat cannot be identified in frequency domain.

The control host 9 is used to receive the confirmed signal Sc from the wearable accessary 400 and perform the aforementioned individualized control associated with the user ID according to the confirmed signal Sc being received.

In one non-limiting embodiment, when the wearable accessary 400 receives the ID signal Sp and the heartbeat is continuously detectable, a confirmed state, meaning a legal user being confirmed, is activated. The control host 9 is used to receive a confirmed signal Sc from the wearable accessary 400 after the wearable accessary 400 activates the confirmed state, and to perform the individualized control associated with the user ID according to the confirmed signal Sc. That is, the wearable accessary 400 outputs the confirmed signal Sc only after the ID signal Sp is received.

While the confirmed state is active, the wearable accessary 400 sends the confirmed signal Sc when receiving a request from the control host 9. For example, the control host 9 receives the confirmed signal Sc through a Bluetooth communication, a radio frequency identification (RFID) technique or other wireless communication techniques. In one embodiment, when the control host 9 sends a request for constructing a Bluetooth communication, the wearable accessary 400 accepts and builds up a linkage with the control host 9 (e.g., Bluetooth pairing being performed previously). After the communication is constructed, the wearable accessary 400 transmits the confirmed signal Sc to the control host 9. In another embodiment, the wearable accessary 400 is integrated with a RFID tag, and the control host 9 generates microwaves to the RFID tags to cause the tags to respond the confirmed signal Sc to the control host 9.

In this way, even though the portable device 300 is not available on hand, the user uses the wearable accessary 400 as an electronic key to actively or passively transmit the confirmed signal Sc to the control host 9 as long as the user continuously wears the wearable accessary 400 with his/her body to allow the heartbeat is detectable by the wearable accessary 400. The control host 9 performs the individualized control associated with the user ID after receiving the confirmed signal Sc.

In addition, when the wearable accessary 400 does not detect the heartbeat while the confirmed state is active for a predetermined period of time, it means that the wearable accessary 400 may be taken off from the user who is ID recognized. The predetermined period of time can be very short, for example as soon as the wearable accessary 400 is taken off. And if the heartbeat, under the confirmed state, is not detectable for a predetermined period of time and then detected again, it means that the wearable accessary 400 may be taken off from the user who is ID recognized and then worn by another user who is not yet ID confirmed by the portable device 300, and thus the confirmed state is preferably also left. If it is desired to activate the confirmed state again, another ID recognition performed by the portable device 300 is necessary. Accordingly, a higher security is achieved.

The control host 9 includes, for example, a microcontroller (MCU), a central processing unit (CPU) or a specific application integrated circuit (ASIC) that executes the functions thereof by hardware and/or software. The functions are determined according to the equipment or system controlled thereby.

In addition, after the wearable accessary 400 receives the ID signal Sp or the confirmed state is activated, the wearable accessary 400 selects to transmit a signal in response to the portable device 300 that the ID signal Sp has been received to cause the portable device 300 to stop outputting the ID signal Sp, but not limited thereto. In other embodiments, the wearable accessary 400 sends a signal to the portable device 300 to cause the portable device 300 to stop outputting the ID signal Sp after the confirmed signal Sc is transmitted.

Referring to FIG. 13B, it is a schematic diagram of an individualized control system according to an alternative embodiment of the present disclosure. The individualized control system also includes a portable device 300, a wearable accessary 400 and a control host 9.

In this embodiment, the portable device 300 includes a Bluetooth device 301, wherein an arranged position of the Bluetooth device 301 in FIG. 13B is only intended to illustrate but not to limit the present disclosure. The portable device 300 is also used to detect a biometric characteristic to identify a user ID according to the biometric characteristic, wherein the biometric characteristic is similar to those mentioned above. The portable device 300 turns on the Bluetooth device 301 when the user ID is confirmed, wherein details of the portable device 300 for detecting the biometric characteristic and confirming the user ID have been illustrated above, and thus are not repeated herein. The difference between this embodiment and the previous embodiment is that in this embodiment the portable device 300 turns on the Bluetooth device 301 to require a construction of a Bluetooth link (e.g., Bluetooth pairing being done previously) with the wearable accessary 400 after the user ID is confirmed.

In this embodiment, the wearable accessary 400 is also used to detect a heartbeat e.g., including a detection module 10' whose detection method has been described above. When a Bluetooth link between the wearable accessary 400 and the portable device 300 is accomplished and a heartbeat is continuously detectable, the wearable accessary 400 transmits a confirmed signal Sc to the control host 9. It is appreciated that the wearable accessary 400 also has a Bluetooth device 401 used to form the Bluetooth connection.

In this embodiment, the wearable accessary 400 activates a confirmed state after the Bluetooth link is formed so as to actively or passively send the confirmed signal Sc, wherein an active way is to repeatedly transmit at a transmission frequency using a wireless communication technique, and the passive way has been described by examples in the previous embodiment such as using Bluetooth communication or RFID.

In the present disclosure, the confirmed state is referred to that the wearable accessary 400 is ready to output, actively or passively, the confirmed signal Sc. It should be mentioned that the confirmed state is not referred to a specific state entered by performing a special operation with the wearable accessary 400. The confirmed state being left is referred to that the confirmed signal Sc is not outputted unless a next ID signal Sp is received by the wearable accessary 400.

Similarly, the control host 9 is used to receive a confirmed signal Sc from the wearable accessary 400 after the wearable accessary 400 activates the confirmed state, and performs the individualized control associated with the user ID according to the confirmed signal Sc being received.

In a brief, a difference between FIGS. 13A and 13B is that in FIG. 13B, after the Bluetooth link is constructed, the wearable accessary 400 identifies the ID recognition being accomplished and thus the confirmed signal Sc is transmitted to the control host 9.

In addition, when the wearable accessary 400 finishes the Bluetooth link or activates the confirmed state, the Bluetooth link is selected to be released to reduce the total power consumption of the system, but not limited thereto.

In this embodiment, the wearable accessary 400 is also used as an electronic key to improve the user experience.

As mentioned above, the individualized control system in embodiments of FIGS. 13A and 13B uses the confirmed signal Sc sent by the wearable accessary 400 to inform the control host 9 to perform the individualized control, and this is different from the above embodiments in which the ID signal Sp is used to inform the control host 9 to perform the individualized control. In FIGS. 13A and 13B, the ID signal Sp is sent to the wearable accessary 400. That is, the control host 9 performs a home appliance control, a power system control, a vehicle device control, a security system control and a warning device control based on the confirmed signal Sc rather than the ID signal Sp.

In other embodiments, the control host 9 is arranged in a way that when anyone of the confirmed signal Sc and the ID signal Sp is receive, the individualized control is performed.

In an alternative embodiment, the portable device 300 in FIGS. 13A and 13B is replaced by a work station. The work station is located, for example, at an entrance or a gate of a building. Any one intended to enter the building needs to finish a security check at the work station. Accordingly, the work station includes a detection module used to detect a fingerprint, an iris, a face, a voiceprint, an atrial fibrillation, PPG, EGC, HRV or SDPPG as that described in the portable device 300 mentioned above. The work station includes any suitable computer system used to perform the detection based on built in hardware and/or software codes.

In this embodiment, when the work station confirms the user ID according to the specific feature(s) of a person, the work station generates a ID signal Sp.

In this embodiment, a wearable accessary such as 400 in FIGS. 13A and 13B is used to detect a heartbeat and receive the ID signal Sp sent from the work station. When receiving the ID signal Sp and continuously detecting the heartbeat, the wearable accessary sends a confirmed signal Sc to a control host such as 9 in FIGS. 13A and 13B.

The control host is used to receive the confirmed signal Sc from the wearable accessary and perform the aforementioned individualized control associated with the user ID according to the confirmed signal Sc being received. In one non-limiting embodiment, the control host preferably has multiple receivers arranged at different rooms and spaces of the building for receiving the confirmed signal Sc at different places. The type of the receivers is determined according to the communication between the wearable accessary and the control host. For example, if the RFID based communication is used, the receivers are RFID signal receivers; and if the Bluetooth based communication is used, the receivers are Bluetooth devices. In another non-limiting embodiment, the building is disposed with multiple control hosts at different rooms and spaces. The control host performs different individualized controls as those mentioned above at different places according to functions of said different rooms or places.

In addition, in a room or space that a person wearing the wearable accessary is required to take off the wearable accessary from time to time, preferably another work station is arranged in that room or space as an auxiliary check point for the person to recheck his/her ID for triggering the wearable accessary again.

In brief, the individualized control system in this embodiment includes a work station, a wearable accessary and a control host. In addition to that the work station is generally set at a fixed spot which is different from the portable device 300, operations of the work station, the wearable accessary and the control host in this embodiment are respectively similar to the portable device 300, wearable accessary 400 and control host 9 in FIGS. 13A and 13B. The work station in this embodiment at least includes a detection module for detecting the biometric characteristic, a processor for identifying a user ID according to the biometric characteristic, and a wireless communication device for transmitting the ID signal to the wearable accessary.

In one non-limiting embodiment, the work station is a part of the control host, or coupled with the control host. And when the work station identifies a user ID, the control host is informed with which person has been identified.

In one non-limiting embodiment, the vehicle device control includes starting a vehicle using the confirmed signal Sc. In one non-limiting embodiment, the security system control includes unlocking a security system using the confirmed signal Sc. The home appliance control includes turning on at least one appliance with a predetermined user setting using the confirmed signal Sc. The power system control includes turning on cameras, light sources, fans or other devices in a particular area using the confirmed signal Sc.

The wearable accessary 400 further detects an attached status with a user to determine whether the wearable accessary 400 is properly worn by the user to improve confidence of the detected result. Many technologies can be applied to perform this function. Such as by using a pressure sensor to detect the tension of a belt for fixing the wearable accessary 400 on the user's body, or to detect the pressure on the user's skin when the wearable accessary 400 is wear tightly. Or, by using a capacitive sensor to detect the proximity between the wearable accessary 400 and the user's skin, the attached status is confirmable. Or, by using a humidity sensor to detect the slight sweat between the wearable accessary 400 and user's skin, the attached status is confirmable. Or, by using a thermal sensor to detect the temperature change between the wearable accessary 400 and user's skin, the attached status is confirmable.

In order to determine whether the attached status is good or not, a processor of the wearable accessary 400, e.g., a digital processing unit (DSP) or an application specific integrated circuit (ASIC), compares the detected result (e.g., including pressure, capacitance change, humidity or temperature) of the above sensors with a predetermined threshold, which is previously determined corresponding to a type of sensor. When a variation of the detected result exceeds the predetermined threshold, the attached status is determined to have a change between an attached state and a lift up state.

In other aspects, the wearable accessary 400 confirms the attached status by analyzing intensity of light passing through different polarizers and detected by the detection module 10, by analyzing intensity of different light wavelengths detected by the detection module 10, by analyzing intensity distribution of an image frame detected by the detection module 10, and by calculating a time-of-flight according to signals (e.g., avalanche current) detected by a single photon avalanche photodiode (SPAD).

When the user removes the wearable accessary 400 from his/her body, the wearable accessary 400 can then detect the status change, and stops generating the confirmed signal if a lift up state is confirmed.

In the above embodiments, the portable device is arranged to identify a user ID according to the biometric characteristic of the user. In an alternatively embodiment, the portable device is arranged to identify the user ID according to a user input which includes a password, a gesture, knocks and/or a speech sentence. One difference between this embodiment and the above embodiments is that the biometric characteristic being detected by the portable device is replaced by the user input. Other operations of the portable device are identical to those in the above embodiments, and thus details thereof are not repeated herein.

In an aspect that uses the password as a user input, the portable device includes a keyboard or a touch panel to receive a set of password inputted by a current user. The portable device then compares the inputted password with a set of pre-stored password to confirm the user ID of the current user. The pre-stored password is preferably set or selected by the same user in a setting procedure and stored in a memory of the portable device.

In an aspect that uses the gesture as a user input, the portable device includes a touch panel or an optical gesture detector to detect a gesture inputted by a current user, e.g., using his or her finger(s). For the touch panel, the current user draws the gesture on the touch panel; whereas for the optical gesture detector, the user draws the gesture (e.g., moving finger) in the space in front of the optical gesture detector. The portable device then compares the inputted gesture with a pre-stored gesture to confirm the user ID of the current user. The pre-stored gesture is preferably set or performed by the same user in a setting procedure and stored in a memory of the portable device.

In an aspect that uses the knocks as a user input, the portable device includes a gyro or a 2D or 3D acceleration sensor to detect knocking signals inputted by a current user. The portable device then compares the inputted knocking signals with pre-stored knocking signals to confirm the user ID of the current user. The pre-stored knocking signals have a predetermined pattern. As long as the inputted knocking signals have a same pattern with the predetermined pattern, the portable device confirms the user ID. The pre-stored knocking signals (or predetermined pattern) is preferably inputted or performed by the same user in a setting procedure and stored in a memory of the portable device.

In an aspect that uses the speech sentence as a user input, the portable device includes a microphone to receive a speech sentence said by a current user. The portable device then compares the said speech sentence (including numbers and/or words) with a pre-stored speech sentence to confirm the user ID of the current user. The pre-stored speech sentence is preferably inputted or recorded by the same user in a setting procedure and stored in a memory of the portable device. That is, the portable device has the language processing function to process the speech sentence inputted via the microphone and identifies whether the inputted speech sentence matches a predetermined speech sentence, like an audio password, to identify the user ID.

Another difference between this embodiment and the above embodiments is that the continuously detected heartbeat is replaced by continuously detected attached status. The attached status is detected by detecting at least one of a heartbeat, capacitance using a capacitive sensor, light intensity using an optical sensor, a temperature using a thermal sensor, sweat using a humidity sensor. More specifically, in the above embodiments, the heartbeat being continuously detected is used as one example to refer that the wearable accessary is continuously being worn by a user. Other methods for confirming the wearable accessary being continuously worn are used in this embodiment. The change of the attached status from contact to non-contact is detectable by detecting a value change of the above parameters, including with/without heartbeat, capacitance variation, light intensity variation, capacitance variation, temperature variation, humidity variation or the like. The parameter variation is compared with a predetermined parameter to confirm the change of attached status.

In an alternative embodiment, the continuously detected attached status further includes continuously detecting a respiration signal in the PPG signal, continuously detecting an arc-like pattern in an energy distribution associated with multiple PPG signals, and continuously detecting a signal-to-noise ratio (SNR) of a PPG signal larger than a predetermined SNR threshold. The portable device 300 and the wearable accessary 400 form a detection device of an individualized control system of the present disclosure. The control host 9 of the individualized control system is coupled to the detection device to receive a confirmed signal to perform an individualized control associated with a user ID identified by the detection device.

Figure 14:
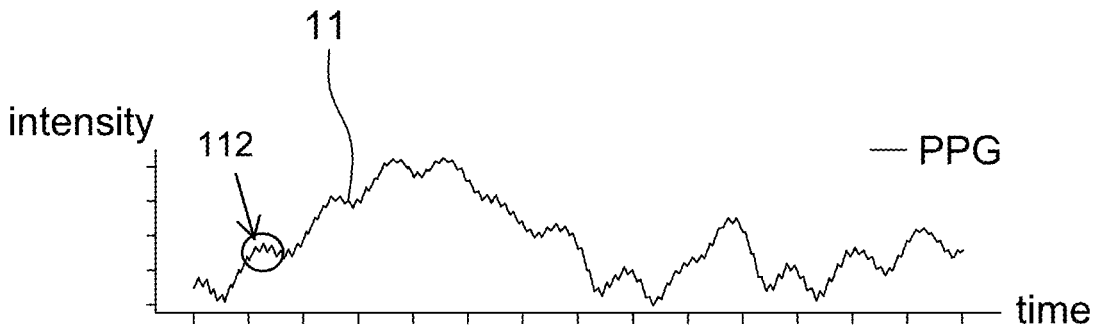
FIG. 14 it is a schematic diagram of a PPG signal detected by a wearable accessary according to one embodiment of the present disclosure.
Figure 15:
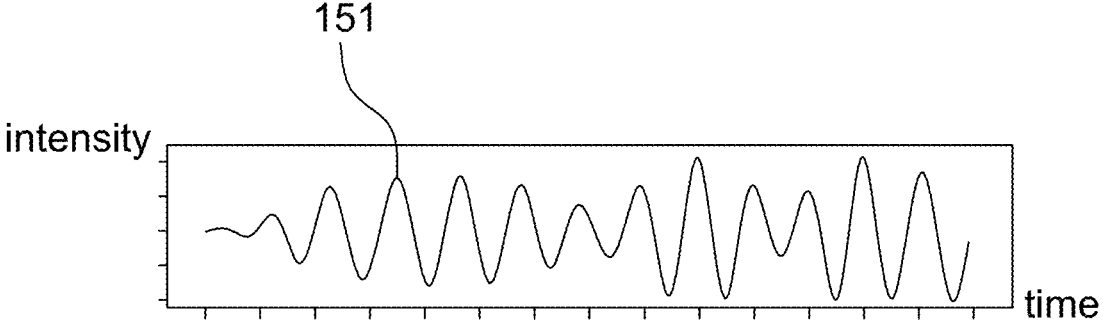
FIG. 15 it is a schematic diagram of a respiration signal retrieved from the PPG signal shown in FIG. 14.

Referring to FIG. 14, it is schematic diagram of a PPG signal detected by the wearable accessary 400, e.g., by the detection module 10' thereof shown in FIG. 2A. In the PPG signal, a high frequency part 112 of the PPG signal 11 indicates a frequency of the heart circulation. A low frequency carrier of the PPG signal 11 is then identified to determine one corresponding low frequency carrier signal, which has a low frequency capable of being used to indicate a breathing signal or respiration signal 151 of a user, as shown in FIG. 15. For example, the wearable accessary 400 (more specifically a processor thereof) acquires the breathing signal or respiration signal 151 from the PPG signal 11 by a digital band pass filter. Generally, a user's respiration rate is lower than 15 times per minute, so a pass band of the digital band pass filter is preferably lower than 0.25 Hz.

For example, when the respiration signal is continuously detected (i.e. attached state) by the wearable accessary 400 according to the PPG signal after the ID signal is received by the wearable accessary 400 from the portable device 300, the wearable accessary 400 sends a confirmed signal to the control host 9, and when the respiration signal is not detected (i.e. lift up state) by the wearable accessary 400 according to the PPG signal, the confirmed signal is not sent to the control host 9.

As mentioned above, it is possible to use the signal-to-noise ratio (SNR) of the PPG signal to determine whether the heartbeat is detectable. Accordingly, in another aspect, the SNR of the PPG signal is directly used to determine whether a wearable accessary 400 is well attached or not. For example, the wearable accessary 400 calculates the SNR of the detected PPG signal. When the calculated SNR of the PPG signal is continuously larger than an SNR threshold (i.e. attached state) after the ID signal is received by the wearable accessary 400 from the portable device 300, the wearable accessary 400 sends a confirmed signal to the control host 9, and when the calculated SNR is not larger (e.g., smaller than or equal to) than the SNR threshold (i.e. lift up state), the confirmed signal is not sent to the control host 9. In this aspect, the SNR threshold is either a fixed predetermined threshold or a threshold real-timely determined or adjusted according to the detected PPG signal.

Figure 16A:
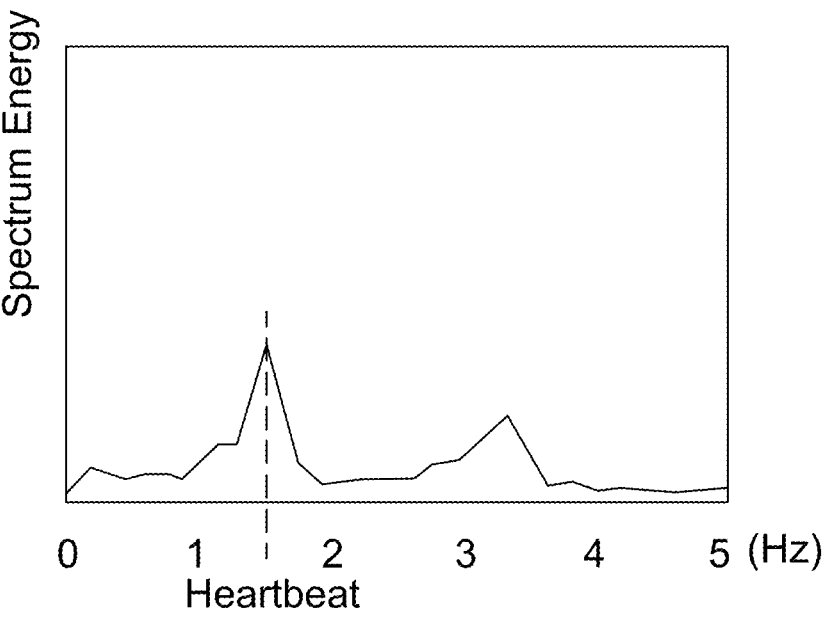
FIG. 16A is a schematic diagram of an energy distribution of the PPG signal shown in FIG. 14.
Figure 16B:
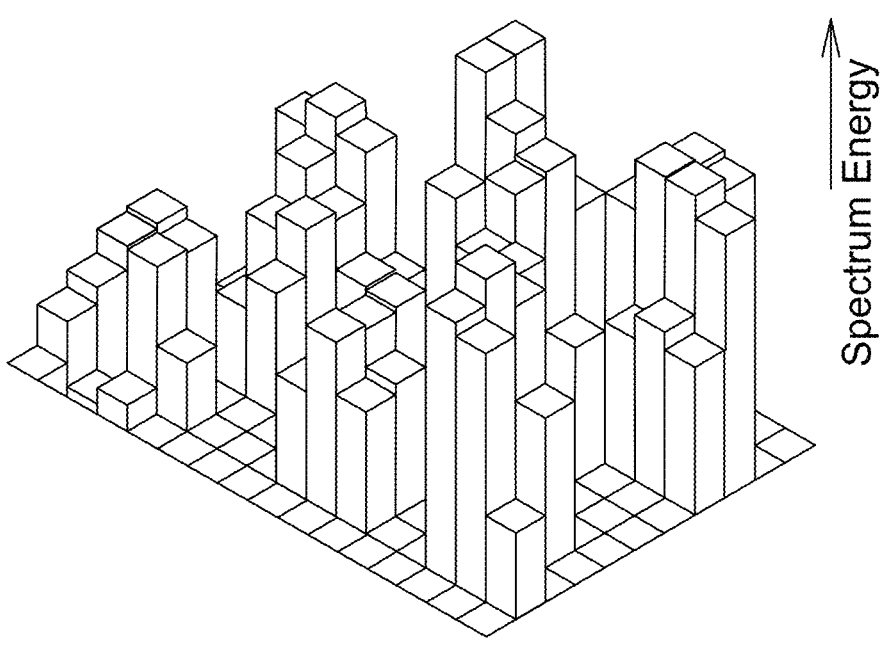
FIG. 16B is a schematic diagram of an energy distribution of spectrum energy associated with PPG signals of multiple pixels or pixel regions of a pixel array according to one embodiment of the present disclosure.

In the case that the wearable accessary 400 includes a pixel array (or the detection module 10' thereof including a pixel array as shown in FIG. 5 to FIG. 6B), each pixel or a pixel region of the pixel array outputs a PPG signal as shown in FIG. 14 as an example, wherein one pixel region includes multiple pixels and PPG signals of each of the multiple pixels in said one pixel region are summed up to obtain one PPG signal sum to improve the SNR of the PPG signal. The PPG signals of every pixel or pixel region are converted (e.g., by Fourier Transform or FFT) into a frequency spectrum as shown in FIG. 16A that contains spectrum energy of multiple frequencies. By distributing these spectrum energy of every pixel, at a selected frequency (e.g., the frequency of heartbeat, but not limited to), on a 2-dimensional (2D) space that corresponds to the pixel array, a 3-dimensional (3D) energy distribution is obtained as shown in FIG. 16B as an example. In FIG. 16B, each bar indicates a spectrum energy at the specific frequency retrieves from the frequency spectrum of the PPG signal associated with one pixel or one pixel region.

Figure 17A:
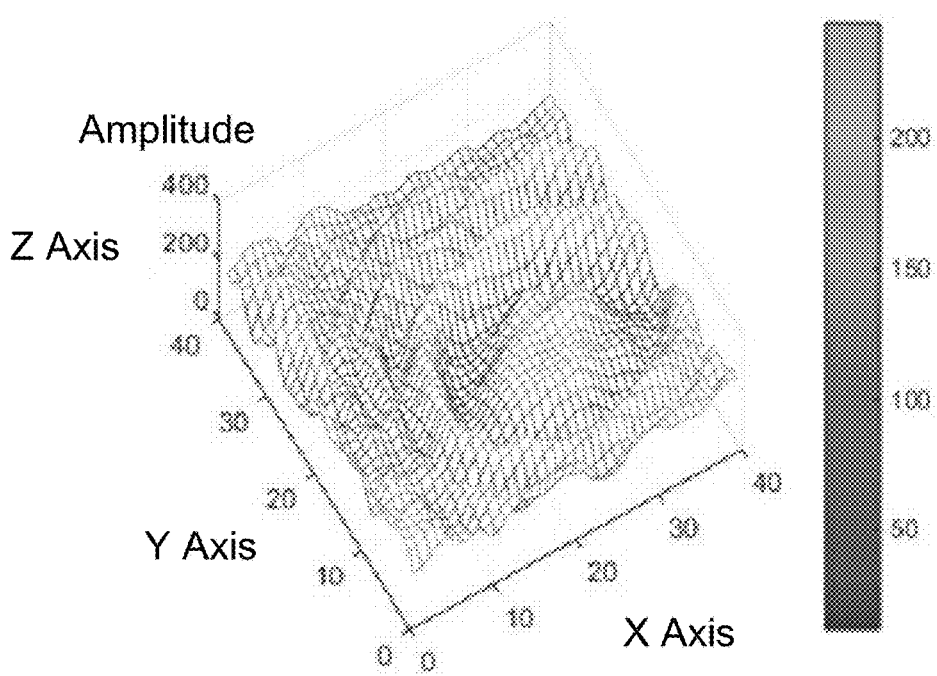
FIGS. 17A and 17B are schematic diagrams of arc-like patterns in the energy distributions according to some embodiments of the present disclosure.
Figure 17B:
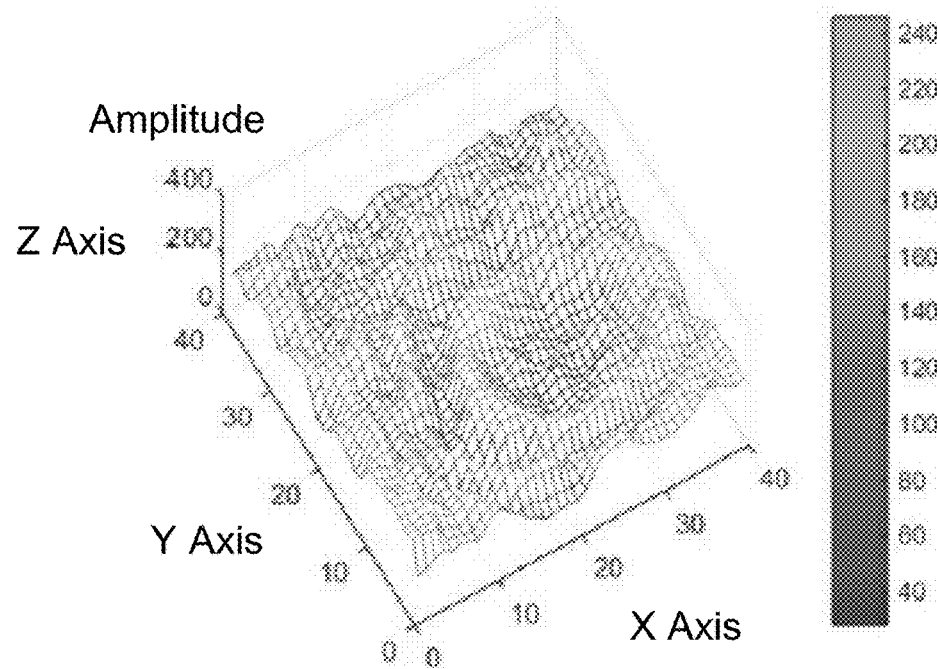

It is noticed that if the wearable accessary 400 is well attached to a skin surface, the 3D energy distribution forms or contains an arc-like pattern as shown in FIGS. 17A and 17B, wherein FIGS. 17A and 17B are two 3D energy distributions obtained at different times (e.g., separated by one sampling period) and alternatively detected by the wearable accessary 400. It is appreciated that each rectangle in FIGS. 17A and 17B indicates the spectrum energy of one pixel or pixel region. In one aspect, the arc-like pattern is applied to evaluate whether the wearable accessary 400 is properly worn by a user.

For example, when the arc-like pattern in the 3D energy distribution is continuously detected (i.e. attached state) by the wearable accessary 400 after the ID signal is received by the wearable accessary 400 from the portable device 300, the wearable accessary 400 sends a confirmed signal to the control host 9, and when the arc-like pattern is not detected (i.e. lift up state) in the 3D energy distribution by the wearable accessary 400, the confirmed signal is not sent to the control host 9.

The way to identify whether an arc-like pattern is existed or not includes, for example, identifying whether the spectrum energy larger than a predetermined energy threshold forms an enclosed peak in the 3D energy distribution or identifying whether the spectrum energy larger than a predetermined energy threshold contain more than one peak circles in the 3D energy distribution. Different ways may be adopted as long as the processor of the wearable accessary 400 identifies the arc-like pattern as shown in FIGS. 17A and 17B.

In this alternative embodiment, only the parameter used to determine the attached state by the wearable accessary 400 is replaced by the respiration signal, the SNR of PPG signal or the arc-like pattern in the 3D energy distribution, and other operations, e.g., those performed by the portable device 300 and the control host 90, are not changed and have been described in the above descriptions.

Conventionally, user-dedicated information is always stored in the portable device. However, in some scenarios, the portable device may be shared by multiple persons. For example, in a factory, a computer is shared by several shift engineers, and information used by different shift engineers is different from each other. Some information should be used by a specific shift engineer only and not be seen by other shift engineers.

Accordingly, the present disclosure further provides an individualized control system in which the user-dedicated information is not always stored in the portable device, but is downloaded from an external cloud via a network when the portable device is used. In this way, one user will not see any information that is not supposed to be seen to improve the data security. Furthermore, in a scenario that the portable device is lost, the user needs not to worry about the data leakage since the lost portable device does not contain any personal information. Accordingly, the individualized control system and detection device thereof with high security is realized.

Referring to FIGS. 13A and 13B again, in addition to the portable device 300, the wearable accessary 400 and the control host 9, the individualized control system of the present disclosure further includes a system server 500 coupled to the portable device 300 via a network, which includes at least one of a local area network, a wireless network and a satellite network. The types of the portable device 300 and the wearable accessary 400 have been illustrated above, and thus details thereof are not repeated herein.

In one aspect, the system server 500 is a server of a factory or an office, and the portable device 300 is coupled to the system server 500 via, e.g., a Bluetooth network, a WiFi network and/or a local area network.

In another aspect, the system server 500 is a server of a telecom company, and the portable device 300 is coupled to the system server 500 further via, e.g., a wireless network and/or a satellite network. The network used to couple the portable device 300 and the system server 500 is not particular limited as long as information/data can be communicated therebetween in a wired and/or wireless manner.

In one aspect, the portable device 300 detects a biometric characteristic to identify a user ID according to the biometric characteristic. As mentioned above, the biometric characteristic is selected from the group consisting of a fingerprint, an iris, a face, a voiceprint, an atrial fibrillation, a heart rate variability and a second derivative of photoplethysmogram. The portable device 300 then outputs an ID signal Sp associated with the identified user ID. Details of identifying the user ID according to the biometric characteristic so as to output the ID signal Sp correspondingly have been illustrated above, and thus are not repeated herein. In this aspect, the ID signal Sp is not only received by the wearable accessary 400 but also received by the system server 500.

The system server 500 is coupled to a cloud via a network, wherein the network also includes at least one of a local area network, a wireless network and a satellite network. In one aspect, the cloud is formed by the storage device or equipment of the system server 500, and the network is an internal network of the system server 500. In another aspect, the cloud is formed by the storage device or equipment anywhere outside the system server 500.

The system server 500 receives the ID signal Sp from the portable device 300, and downloads information associated with the identified user ID from the cloud to the portable device 300 if the cloud has recorded the associated information. In this aspect, the information includes an audio file, an edited document, a device setup file, an APP, a working log, a calendar, storage data, an address book or other dedicated data associated with the identified user ID. The portable device 300 downloads information associated with the identified user ID from the cloud via the system server 500 every time a user ID being identified by the portable device 300, and updated information is uploaded to the cloud via the system server 500 when the user is logged out from portable device 300 or the attached status of the wearable accessary 400 is fail.

It is appreciated that when the cloud does not contain any information associated with the identified user ID or the system server 500 confirms that the identified user ID is not a valid ID, the system server 500 does not download any information to the portable device 300.

As mentioned above, in some aspects the portable device 300 is operable only when the wearable accessary 400 is continuously worn by a user associated with the identified user ID. To detect the wearing state (i.e. attached status mentioned above) of the wearable accessary 400, the wearable accessary 400 detects, for example, a respiration signal in a photoplethysmogram (PPG) signal, a heartbeat in the PPG signal, an arc-like pattern in an energy distribution associated with multiple PPG signals or a signal-to-noise ratio (SNR) of the PPG signal, wherein details of detecting the attached status have been illustrated above, and thus are not repeated herein. In addition to send the confirmed signal Sc after the ID signal Sp is received from the portable device 300 and the respiration signal, the heartbeat or the arc-like pattern is continuously detected or the SNR is continuously larger than a SNR threshold to indicate that the wearable accessary 400 is properly worn by the user (i.e. attached status is positive), the wearable accessary 400 further sends a lock signal $S_{Lock}$ to the portable device 300 to lock the portable device 300 after the ID signal Sp is received from the portable device 300 and when the attached status indicates a lift up state. When the portable device 300 is locked, it is not operable until a next ID recognition is finished.

In one aspect, the portable device 300 further uploads updated information associated with the identified user ID to the cloud via the system server 500 and cleans the downloaded information therein after receiving the lock signal $S_{Lock}$ from the wearable accessary 400. In this way, the portable device 300 does not record any user-dedicated information when there is no one operating the portable device 300 or the wearable accessary 400 is not worn properly. To continuously operate the portable device 300, the user needs to perform another ID recognition to cause the portable device 300 to send the ID signal Sp to the wearable accessary 400 and the system server 500 again.

As mentioned above, the portable device 300 may further identify the user ID according to a user input such as a password, a gesture, knocks and/or a speech sentence. Details of identifying the user ID according to the user input have been illustrated above, and thus are not repeated herein.

In an alternatively aspect, the portable device 300 does not identify the user ID but only detects a biometric characteristic and outputs the detected biometric characteristic to the system server 500. The system server 500 receives the biometric characteristic from the portable device 300, identifies a user ID according to the received biometric characteristic, and downloads information associated with the identified user ID from the cloud to the portable device 300. Preferably, the system server 500 (or on the cloud) previously records biometric characteristics of at least one predetermined user ID, and when receiving the biometric characteristic from the portable device 300, the system server 500 compares the received biometric characteristic with the recorded biometric characteristics. If a match is reached, the user ID is confirmed and the system server 500 downloads the information associated with the matched predetermined user ID from the cloud to the portable device 300.

In this aspect, the wearable accessary 400 identifies the user ID according to the received biometric characteristic. If a valid user ID is confirmed, the wearable accessary 400 performs the functions mentioned above, e.g., sending a confirmed signal Sc. The only difference of this aspect is that the user ID is identified by the wearable accessary 400 instead of by the portable device 300, and other operations are not changed.

Similarly, in this aspect, the portable device 300 does not identify the user ID according to the user input. The portable device 300 only detects and outputs a user input to the system server 500, and the system server 500 further identifies the user ID according to the received user input. Preferably, the system server 500 (or on the cloud) previously records user inputs of at least one predetermined user ID, and when receiving the user input from the portable device 300, the system server 500 compares the received user input with the recorded user inputs. If a match is reached, the user ID is confirmed and the system server 500 downloads the information associated with the matched predetermined user ID from the cloud to the portable device 300.

Similarly, the wearable accessary 400 identifies the user ID according to the received user input. If a valid user ID is confirmed, the wearable accessary 400 performs the functions mentioned above, e.g., sending a confirmed signal Sc.

The only difference of this aspect is that the user ID is identified by the wearable accessary 400 instead of by the portable device 300, and other operations are not changed.

The operation (i.e. individualized control) of the control host 9 according to whether the confirmed signal Sc is received from the wearable accessary 400 has been described above, and thus details thereof are not repeated herein.

In an alternative aspect, the portable device 300 is replaced by a work station, and user-dedicated information is stored in an external cloud and will be downloaded from the external cloud after the work station accomplished the ID recognition. In this way, the data security of the work station is improved.

In one non-limiting aspect, the system server 500 is integrated with or combined with the control host 9 for downloading information from cloud and performing the individualized control according to the identified user ID.

Figure 18A:
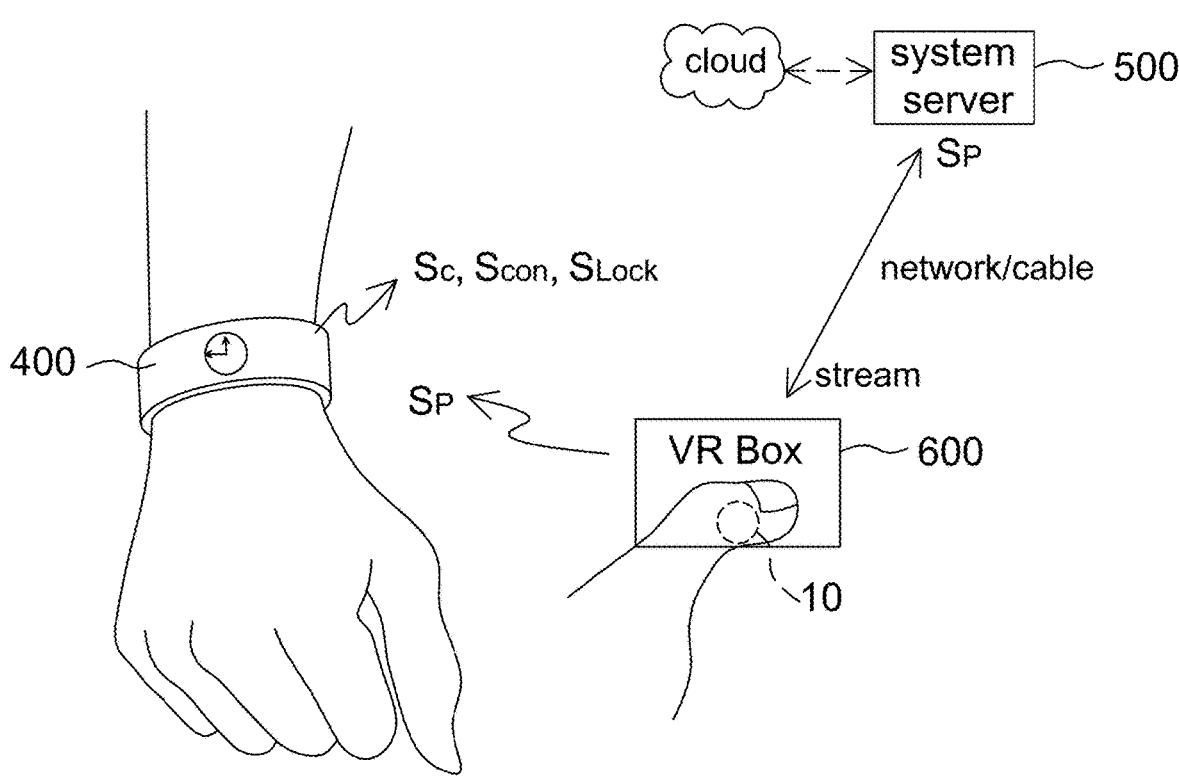
FIGS. 18A and 18B are schematic diagrams of VR systems according to some embodiments of the present disclosure.

Referring to FIG. 18A, it is a schematic diagram of a virtual reality (VR) system according to one embodiment of the present disclosure. The VR system includes a VR box 600, a wearable accessary 400 and a system server 500 coupled to the VR box 600 via a cable line, or via a network, which includes at least one of a local area network, a wireless network and a satellite network. The VR box 600 is VR glasses or a VR goggle that shows video stream or images to be watched by a user. The wearable accessary 400 has been illustrated above, and thus details thereof are not repeated herein. Briefly speaking, the portable device 300 in the embodiment of FIG. 13A is replaced by a VR box 600 in the embodiment of FIG. 18A. Similar to the individualized control system in FIG. 13A, the VR box 600 of the VR system in FIG. 18A downloads data, such as video stream, from the system server 500 after the user ID is confirmed thereby and the wearable accessary 400 is continuously worn by a user.

In one aspect, the system server 500 is a server of game, online shopping platform, streaming service, a factory or an office, and the VR box 600 is coupled to the system server 500 via, e.g., a cable line, a Bluetooth network, a WiFi network and/or a local area network. The system server 500 is not necessary to be arranged at the same room/space with the VR box 600. In the aspect that the VR box 600 is coupled to the system server 500 via an internet, the VR box 600 is considered to be directly coupled to the internet to receive the stream (including audio and video stream) from the internet.

The network used to couple the VR box 600 and the system server 500 is not particular limited as long as information/data can be communicated therebetween in a wired and/or wireless manner.

In one aspect, the VR box 600 detects a biometric characteristic to identify a user ID according to the biometric characteristic, e.g., detected by a biometric detection module 10. As mentioned above, the biometric characteristic is selected from the group consisting of a fingerprint, an iris, a face, a voiceprint, an atrial fibrillation, a heart rate variability and a second derivative of photoplethysmogram. The biometric detection module 10 of the VR box 600 is selected according to the biometric characteristic to be detected, such as a fingerprint detector, an image sensor, a microphone, a PPG detector, a ECG detector as mentioned above. The VR box 600 then outputs an ID signal Sp, in a wired and/or wireless manner, associated with the identified user ID to indicate a valid user is confirmed. An invalid user (not registered in the system server 500) is not allowed to operate the VR box 600. Details of identifying the user ID according to the biometric characteristic so as to output the ID signal Sp correspondingly have been illustrated above, and thus are not repeated herein. In this aspect, the ID signal Sp is not only received by the wearable accessary 400 but also received by the system server 500.

The system server 500 is coupled to a cloud and/or another VR box via a network, wherein the network also includes at least one of a local area network, a wireless network and a satellite network. In one aspect, the cloud is formed by the storage device or equipment of the system server 500, and the network is an internal network of the system server 500. In another aspect, the cloud is formed by the storage device or equipment anywhere outside the system server 500. Said another VR box, which is also coupled to or not coupled to another wearable accessary, interacts with the VR box 600 via the system server 500.

The system server 500 receives the ID signal Sp from the VR box 600, and transmits video stream associated with the identified user ID to the VR box 600 to be shown thereon, i.e. the ID signal Sp is used as an request for acquiring the video stream. In one aspect, the video stream associated with the identified user ID herein is referred to those dedicated only to the identified user ID, and the dedicated video stream is not transmitted from the system server 500 to the VR box 600 if the ID signal Sp is not sent from the VR box 600 and received by the system server 500. In another aspect, the video stream transmitted from the system server 500 to the VR box 600 is not dedicated to the identified user ID, and is arranged to be watched by any user who passes the ID recognition, i.e. valid user. More specifically, if the VR box 600 can be operated or used by multiple persons (i.e. multiple valid users), each user can watch the dedicated video stream and common shared video stream provided from the system server 500. For example, the authority is pre-set in the system server 500, which determines the video stream to be transmitted by comparing the ID signal Sp and the authority.

In this embodiment, the video stream is associated with a video game, online meeting, online shopping and web tutorial associated with the identified user ID, or not associated with the identified user ID. The video stream is stored in the system server 500 or downloaded from a cloud or a media platform. It should be mentioned that the video stream is not limited to images or pictures, but includes files, documents and other digital data as long as they are shown by the VR box 600.

As mentioned above, in some aspects the VR box 600 is operable only when the wearable accessary 400 is continuously worn by a user associated with the identified user ID. In this case, the wearable accessary 400 is used as means for controlling and interacting with the VR box 600. To detect the wearing state (i.e. attached status mentioned above) of the wearable accessary 400, the wearable accessary 400 detects, for example, a respiration signal in a PPG signal, a heartbeat in the PPG signal, an arc-like pattern in an energy distribution associated with multiple PPG signals, an SNR of the PPG signal and other features mentioned above, and thus are not repeated herein.

In addition to send the confirmed signal Sc after the ID signal Sp is received from the VR box 600 and the respiration signal, the heartbeat or the arc-like pattern is continuously detected or the SNR is continuously larger than a SNR threshold to indicate that the wearable accessary 400 is properly worn by the user (i.e. attached status is positive), the wearable accessary 400 further sends a lock signal $S_{Lock}$ to the VR box 600 to lock the VR box 600 after the ID signal Sp is received from the VR box 600 and when the attached status indicates a lift up state. When the VR box 600 is locked, it is not operable until a next ID recognition is accomplished.

In this aspect, the wearable accessary 400 detects an attached status, as mentioned above, and further detects movement of the wearable accessary 400 after receiving the ID signal from the VR box. When the attached status indicates continuous wearing, the wearable accessary 400 sends a control signal Scon, associated with the detected movement, to the system server 500 to change image content in the video stream according to the detected movement of the wearable accessary 400. For example, the wearable accessary 400 includes a G-sensor that detects a 2D- or 3D-motion of the wearable accessary 400 in space as the movement. The image content is, for example, a cursor, an object image, a game character or an icon contained in the video stream, and the detected movement is configured to change at least one of a position and a viewing angle of the image content. The movement also triggers a single or double click operation on the image content, e.g., depending on pre-set types of movement.

In this embodiment, the wearable accessary 400 needs not to appear inside a view of the VR box 600 to control the image content in the video stream such that a user only moves the wearable accessary 400 with any comfort posture to reduce user's physical loading in long time operation.

In one aspect, after receiving the lock signal $S_{Lock}$ from the wearable accessary 400, the VR box 600 stops receiving the video stream from the system server 500, or the VR box 600 sends a request to the system server 500 to stop the video stream transmission. In this way, the VR box 600 does not receive any video stream from the system server 500 when there is no one operating the VR box 600 (i.e. no biometric characteristic being detected) or the wearable accessary 400 is not worn properly. To continuously operate the VR box 600, the user needs to perform another ID recognition to cause the VR box 600 to send another ID signal Sp to the wearable accessary 400 and the system server 500 again. In another aspect, the lock signal $S_{Lock}$ is sent to the system server 500, not received by the VR box 600, to stop the video stream transmission.

As mentioned above, the VR box 600 may further identify the user ID according to a user input such as a password, a gesture, knocks and/or a speech sentence. Details of identifying the user ID according to the user input have been illustrated above, and thus are not repeated herein.

In another aspect, the wearable accessary 400 sends a control signal Scon to the VR box 600 to change predetermined image content in the video stream according to the detected movement of the wearable accessary 400 when the attached status indicates continuous wearing. In this aspect, the video stream is pre-arranged with at least one specific image content that can be changed, altered or calibrated, and the system server 500 is not arranged to change, alter or calibrate the specific image content. After receiving the video stream from the system server 500 and the control signal Scon from the wearable accessary 400, the VR box 600 changes the specific image content, such as the position, viewing angle and/or size thereof or performs the click(s) operation according to the control signal Scon.

In an alternatively aspect, the VR box 600 does not identify the user ID but only detects a biometric characteristic and outputs the detected biometric characteristic to the system server 500. The system server 500 receives the biometric characteristic from the VR box 600, identifies a user ID according to the received biometric characteristic, and transmits video stream associated with the identified user ID to the VR box 600 to be shown thereon. Preferably, the system server 500 (or on the cloud) previously records biometric characteristics of at least one predetermined user ID, and when receiving the biometric characteristic from the VR box 600, the system server 500 compares the received biometric characteristic with the recorded biometric characteristics. If a match is reached, the user ID is confirmed and the system server 500 transmits video stream associated with the identified user ID to the VR box 600.

In this aspect, the wearable accessary 400 identifies the user ID according to the received biometric characteristic. If a valid user ID is confirmed, the wearable accessary 400 performs the functions mentioned above, e.g., sending a control signal Scon and a confirmed signal Sc. The only difference of this aspect is that the user ID is identified by the wearable accessary 400 instead of by the VR box 600, and other operations are not changed.

Similarly, in this aspect, the VR box 600 does not identify the user ID according to the user input. The VR box 600 only detects and outputs a user input to the system server 500, and the system server 500 further identifies the user ID according to the received user input. Preferably, the system server 500 (or on the cloud) previously records user inputs of at least one predetermined user ID, and when receiving the user input from the VR box 600, the system server 500 compares the received user input with the recorded user inputs. If a match is reached, the user ID is confirmed and the system server 500 transmits video stream associated with the identified user ID to the VR box 600.

Similarly, the wearable accessary 400 identifies the user ID according to the received user input. If a valid user ID is confirmed, the wearable accessary 400 performs the functions mentioned above, e.g., sending a control signal Scon and a confirmed signal Sc. The only difference of this aspect is that the user ID is identified by the wearable accessary 400 instead of by the VR box 600, and other operations are not changed.

More specifically, the VR box 600 shows video stream only when the wearable accessary 400 is continuously wearing on a valid user after the user ID is identified. Once the wearable accessary 400 is took off from the valid user, the showing function of the VR box 600 is ceased, including not receiving video stream as well as receiving but not showing thereon. The video stream is replayed only after the biometric characteristic or the user input is identified again and the attached status of the indicates continuous wearing.

In should be mentioned that although the above embodiment is illustrated in the way that the system server 500 starts to transmit video stream to the VR box 600 after receiving the ID signal Sp from the VR box 600, the present disclosure is not limited thereto. In another aspect, the system server 500 starts to transmit video stream to the VR box 600 after receiving a confirmed signal Sc from the wearable accessary 400. That is, the ID signal Sp is firstly received by the wearable accessary 400 (but not by the system server 500), and then the wearable accessary 400 sends the confirmed signal Sc after confirming that the attached status indicates continuous wearing.

More specifically, in the VR system in FIG. 18A, the VR box 600 identifies a user ID, and outputs an ID signal Sp associated with the identified user ID; and the wearable accessary 400 detects an attached status and outputs a lock signal $S_{Lock}$ (while took off) and, in some aspects, outputs a confirmed signal Sc. In the case that the confirmed signal Sc is not generated, the system server 500 transmits video stream to the VR box 600 according to the ID signal Sp and stops the transmission according to the lock signal $S_{Lock}$. In the case that the confirmed signal Sc is generated, the system server 500 transmits video stream to the VR box 600 according to the confirmed signal Sc and stops the transmission according to the lock signal $S_{Lock}$. Details of generating the confirmed signal Sc have been illustrated above, and thus are not repeated herein.

Figure 18B:
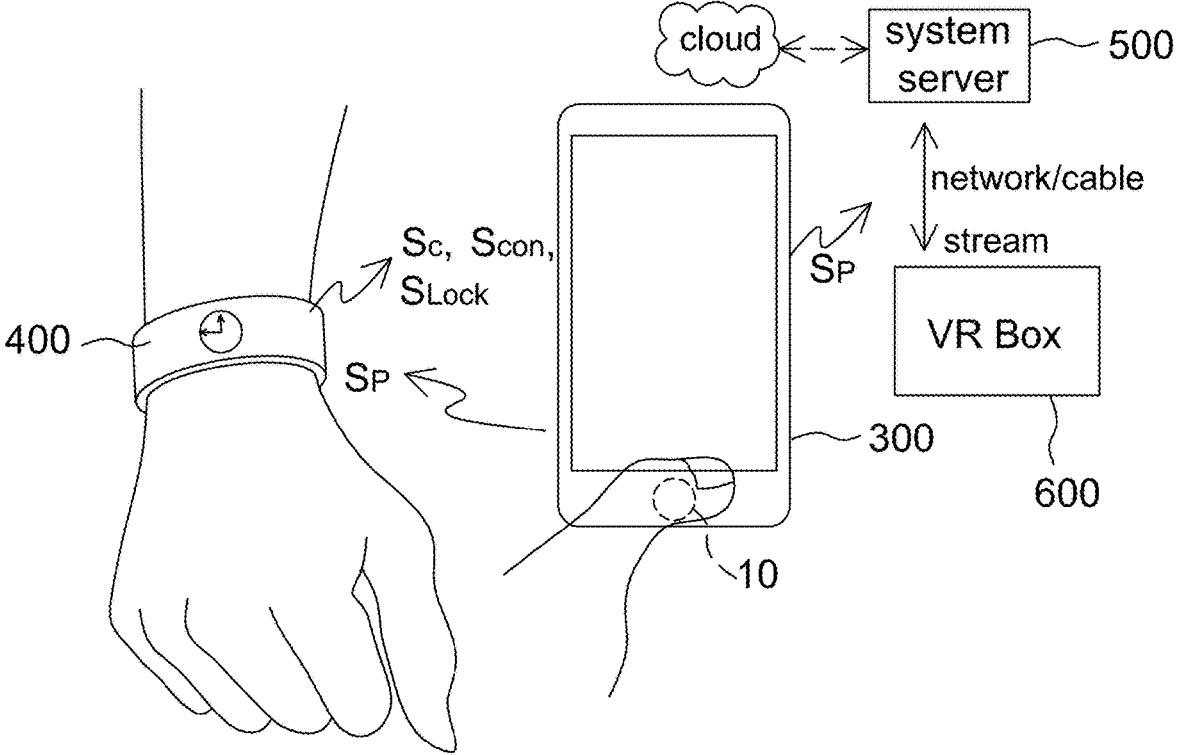

Referring to FIG. 18B, it is a schematic diagram of a virtual reality (VR) system according to another embodiment of the present disclosure. The VR system in FIG. 18B includes a portable device 300, a wearable accessary 400 and a system server 500, similar to FIG. 13A, and further includes a VR box 600. In this embodiment, the portable device 300 and the wearable accessary 400 are identical to those shown in FIG. 13A. In this embodiment, the system server 500 is a server of game, online shop, streaming service, a factory, an office and other servers for interacting with the VR box 600. As mentioned above, the system server 500 transmits video stream to the VR box 600 embedded therein or downloaded from a cloud or a media platform.

As mentioned above, the portable device 300 detects and identifies a user ID according to a biometric characteristic or a user input, and then outputs an ID signal Sp. The wearable accessary 400 receives the ID signal Sp and detects an attached status using the method mentioned above. The wearable accessary 400 is arranged to transmit a confirmed signal Sc or not.

Preferable, before the portable device 300 transmits the ID signal Sp, the VR box 600 and the system server 500 are coupled to each other, wired or wirelessly, and ready to operate, only the video stream still not being transmitted to the VR box 600.

In the case that the wearable accessary 400 does not generate and send the confirmed signal Sc, the system server 500 starts to transmit video stream to the VR box 600 when receiving the ID signal Sp; or the ID signal Sp is received by the VR box 600 and then the VR box 600 transmits a request to the system server 500 to acquire the video stream therefrom. More specifically, the transmission of video stream is started after the ID signal Sp is received by at least one of the VR box 600 and the system server 500.

In the case that the wearable accessary 400 generates and sends the confirmed signal Sc, the system server 500 starts to transmit video stream to the VR box 600 when receiving the confirmed signal Sc; or the confirmed signal Sc is received by the VR box 600 and then the VR box 600 transmits a request to the system server 500 to acquire the video stream therefrom. More specifically, the transmission of video stream is started after the confirmed signal Sc is received by at least one of the VR box 600 and the system server 500.

Similarly, the wearable accessary 400 further detects movement, e.g., of a hand or a leg depending on the position at which the wearable accessary 400 being worn, for controlling image content. For example, the wearable accessary 400 transmits a control signal Scon, associated with the movement, to the system server 500 or the VR box 600 to change the image content in the video stream, details of changing the image content according to the control signal Scon have been illustrated above in the embodiment in FIG. 13A and thus are not repeated.

Similarly, the wearable accessary 400 further detects an attached status with a user skin to confirm whether the video stream is continuously sent from the system server 500 to the VR box 600 or not. The wearable accessary 400 transmits a lock signal $S_{Lock}$ to the system server 500 to cease video stream transmission when a lift up state is detected. Or, the lock signal $S_{Lock}$ is received by the VR box 600, and the VR box 600 actively stops receiving the video stream or sends a request to the system server 500 to stop the video stream transmission. More specifically, after the transmission of video stream is started, the transmission is stopped after the lock signal $S_{Lock}$ is received by at least one of the VR box 600 and the system server 500.

Briefly speaking, the difference between FIG. 18B and FIG. 18A is that the VR box 600 is not functioned as means for detecting and identifying the biometric characteristic. The system servers 500 in FIGS. 18A and 18B both start to transmit video stream to the VR box 600 when a confirmed signal Sc or an ID signal Sp is received thereby, and stop transmitting the video stream, after the transmission being activated, when a lock signal $S_{Lock}$ is received thereby.

In another aspect, the portable device 300 transmits the detected biometric characteristic to the wearable accessary 400 and the system server 500 to be identified thereby, and details thereof have been illustrated above and thus are not repeated herein.

In FIGS. 18A and 18B, the user uses the wearable accessary 400 to interact with (e.g., changing image content mentioned above) the VR box 600 such that the user can operate the VR box 600 easier without getting tired even for a long time operation. Furthermore, the VR box 600 is operable only for a valid (ID identified) user to improve data security. In another aspect, the VR box 600 is further controlled by a pressing signal, a touch signal and/or a rotation signal of the wearable accessary 400 when a key thereon is pressed, a touch pad thereon detects a touch and/or a knob thereon is rotated. The controlled function is pre-set corresponding to different signals.

In addition to showing the video stream received from the system server 500 as mentioned above, the VR box 600 is further arranged to show shared video stream from at least one another VR box (e.g., shown as VR Box II 600' in FIGS. 19A and 19B), wherein the shared video stream is previously provided by said another VR box and recorded in the system server 500, or is real-timely transmitted from said another VR box. The VR box 600' is previously identity authenticated with the VR system shown in FIGS. 18A and 18B. For example, the VR box 600' is authenticated as a friend with the VR box 600, and ID information of the VR box 600' is previously recorded in the system server 500 or the VR box 600 before the VR box 600' shares the image stream (including audio stream) with the VR box 600. For example, the VR box 600' is arranged to broadcasting image stream (including audio stream), and the VR box 600 is authenticated to receive and show the image stream thereon through predetermined authentication method.

In one aspect, the VR box 600' may firstly communicates with a corresponding system server (not shown) and the corresponding system server communicates with the system server 500. In another aspect, the VR box 600' and the VR box 600 share the same system server 500, which is located in an internet coupled to the VR box 600' and the VR box 600. That is, the VR box 600' and the VR box 600 are coupled via the internet, e.g., shown as cloud in FIGS. 19A and 19B.

Figure 19A:
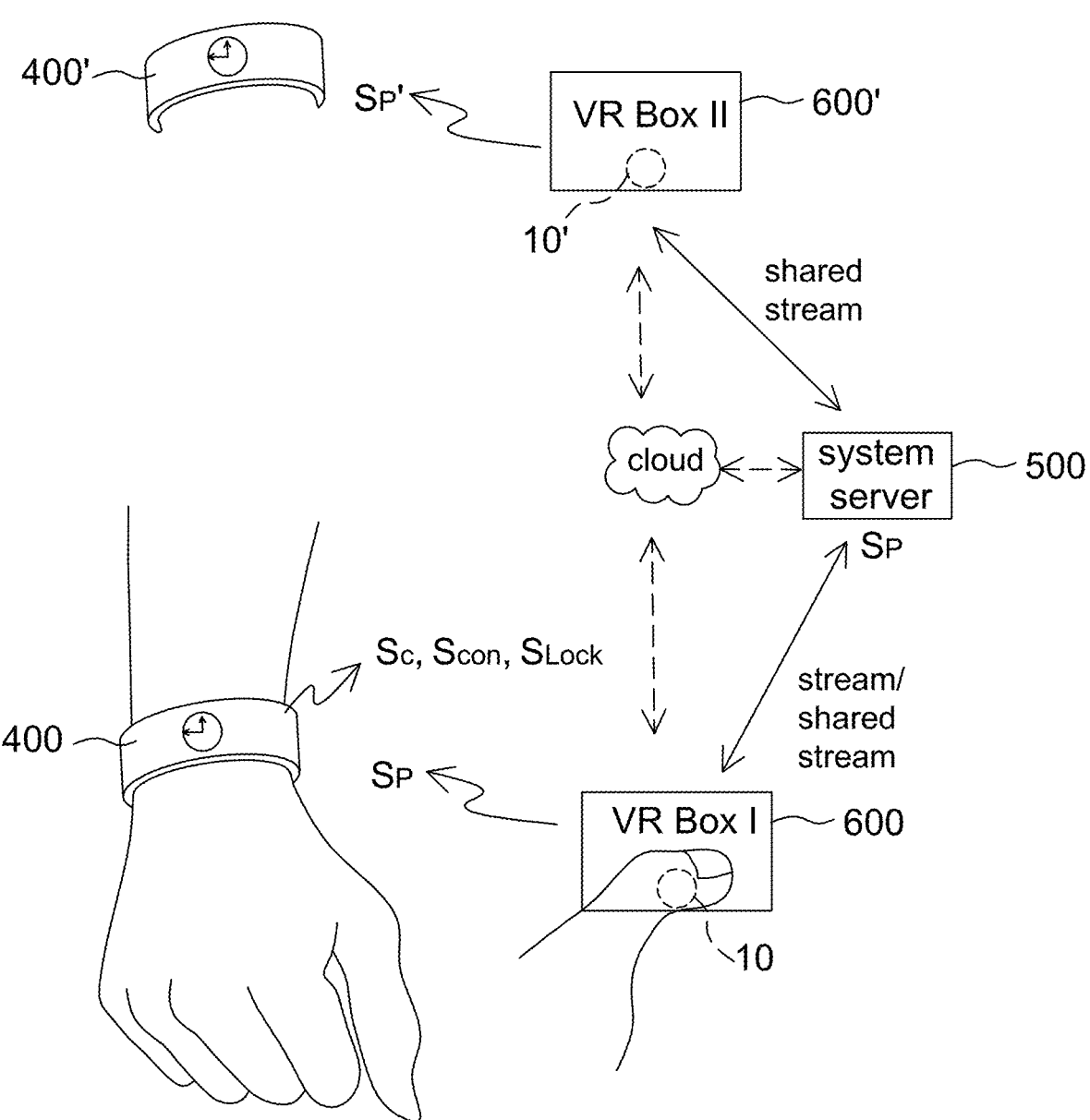
FIGS. 19A and 19B are schematic diagrams of shared VR systems according to some embodiments of the present disclosure.

For example in FIG. 19A, the VR box 600 detects a biometric characteristic to identify a user ID according to the biometric characteristic, and outputs an ID signal Sp associated with the identified user ID. The system server 500 receives the ID signal Sp from the VR box 600, receives shared video stream sharing from another VR box 600' coupled to the system server 500 via an internet, and transmits video stream (not shared from VR box 600') associated with the identified user ID or the shared video stream (shared from VR box 600') to the VR box 600 to be shown thereon. The wearable accessary 400 detects an attached status and movement of the wearable accessary 400 after receiving the ID signal Sp from the VR box 600, and sends a control signal Scon to the image viewing device (e.g., to the system server 500 or the VR box 600 as mentioned above) to change image content to be shown on the VR box 600 as the video stream or the shared video stream according to the detected movement of the wearable accessary 400 when the attached status indicates continuous wearing.

As mentioned above, the detected movement is also used to change at least one of a position and a viewing angle of the image content. Therefore, one movement is used to change the position and the viewing angle, and a different movement (e.g., a different moving direction, a different gesture, a different pattern) is used to control the VR box 600 to show the video stream or to show the shared video stream, i.e. the wearable accessary 400 being used as a switching device for the video stream and the shared video stream. Meanwhile, the lock signal $S_{Lock}$ sent to the image viewing device (e.g., to the system server 500 or the VR box 600 as mentioned above) is used to stop transmission of or playing the video stream or the shared video stream when the attached status indicates a lift up state. The definition and source of the video stream have being described above, and thus details thereof are not repeated again.

For example in FIG. 19A, the VR box 600 detects a biometric characteristic and outputs the biometric characteristic. The system server 500 receives the biometric characteristic to identify a user ID accordingly, receives shared video stream sharing from another VR box 600' coupled to the system server 500 via an internet, and transmits video stream associated with the identified user ID or the shared video stream to the VR box 600 to be shown thereon. The wearable accessary 400 identifies the user ID according to the biometric characteristic received from the VR box 600, detects an attached status and movement of the wearable accessary 400 after confirming a valid user ID, and sends a control signal Scon to the image viewing device (e.g., to the system server 500 or the VR box 600 as mentioned above) to change image content to be shown on the VR box 600 as the video stream or the shared video stream according to the detected movement of the wearable accessary 400 when the attached status indicates continuous wearing.

Similarly, different detected movements are used to change a position and a viewing angle of the image content as well as to switch the image content between the video stream from the system server 500 or the shared video stream from the VR box 600'. Similarly, lock signal $S_{Lock}$ sent to the image viewing device (e.g., to the system server 500 or the VR box 600 as mentioned above) is used to stop transmission of or playing the video stream or the shared video stream when the attached status indicates a lift up state.

In an aspect that the VR box 600 in FIG. 19A is directly coupled to an internet, the VR box 600 identifies a user ID (e.g., using the biometric characteristic or a user input as mentioned above) and outputs an ID signal Sp associated with the identified user ID, receives, from the internet, shared video stream sharing from an imaging device (e.g., shown as VR Box II 600' in FIG. 19A) connected to the internet, and shows video stream associated with the identified user ID or the shared video stream thereon. The wearable accessary 400 detects movement of the wearable accessary 400 after receiving the ID signal Sp from the VR box 600, and sends a control signal Scon to the image viewing device (e.g., to the system server 500 or the VR box 600 as mentioned above) to change image content to be shown on the VR box 600 as the video stream or the shared video stream according to the detected movement of the wearable accessary 400.

Figure 19B:
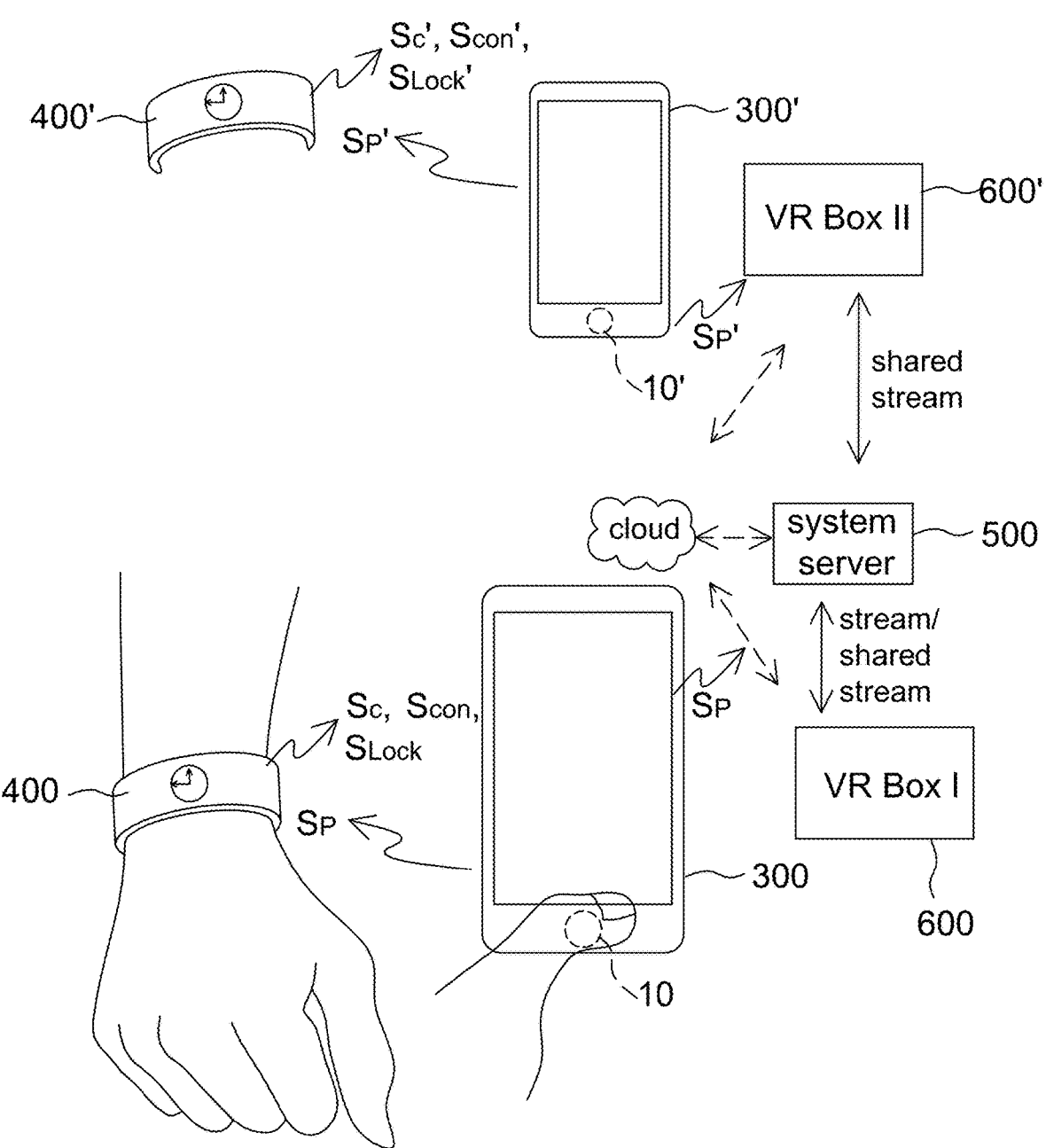

In an aspect that the VR box 600 in FIG. 19B is directly coupled to an internet, the portable device 300 detects and identifies a user ID according to a biometric characteristic or a user input, and then outputs an ID signal Sp associated with the identified user ID. The wearable accessary 400 receives the ID signal Sp and detects an attached status using the method mentioned above. The VR box 600 receives the ID signal Sp associated with the identified user ID or receives the confirmed signal Sc from the wearable accessary 400 (using wireless matter) to start to receive the video stream (not shared from the VR box 600') therefrom. The VR box 600 is directly coupled to an internet to receive shared video stream sharing from an imaging device (e.g., shown as VR Box II 600' in FIG. 19B) connected to the internet. The wearable accessary 400 further detects movement of the wearable accessary 400 after receiving the ID signal Sp from the VR box 600, and sends a control signal Scon to the image viewing device (e.g., to the system server 500 or the VR box 600 as mentioned above) to change image content to be shown on the VR box 600 as the video stream or the shared video stream according to the detected movement of the wearable accessary 400.

In one aspect, said another VR box 600' may send a sharing signal (as a request) to the image viewing device (e.g., to the system server 500 or the VR box 600 as mentioned above) to be shown on the VR box 600 for being confirmed by a user of the VR box 600. For example, the user uses the wearable accessary 400 to confirm whether to switch the image content (i.e. the video stream and the shared video stream) to be shown on the box 600, e.g., according to the detected movement of the wearable accessary 400 as mentioned above.

It should be mentioned that although the present disclosure is described by sharing image streams between two VR boxes, the present disclosure is not limited thereto. In other aspects, the VR box II 600' shown in FIGS. 19A and 19B are replaced by an imaging device which is previously identity authenticated with the VR system shown in FIGS. 18A and 18B, e.g., the VR system shown in FIGS. 18A and 18B being previously receiving ID information and authenticating the imaging device 600' to transmit streams to the VR system.

For example, the imaging device 600' is another VR box, a drone, a smartphone or a camera, such as a web camera or a security camera, having a CMOS image sensor or a CCD image sensor therein. When the imaging device 600' is another VR box (e.g., shown as VR box II 600' in FIGS. 19A and 19B), the operation of the imaging device 600' is identical to the VR Box (e.g., shown as VR box I 600 in FIGS. 19A and 19B) shown in FIGS. 18A and 18B and thus details thereof are not repeated herein. Meanwhile, the another VR box performs all operations run by the VR box 600, including showing streams (including video and audio streams) shared by the VR box 600.

The biometric characteristic is detected by a biometric detection module 10 as mentioned above, and thus details thereof are not repeated herein.

However, when the imaging device 600' is a drone, a smartphone or a camera, the imaging device 600' is not required to operate incorporating with a wearable accessary but is still able to output/transmit shared video stream (including audio information) to the VR box (e.g., directly or via a cloud) 600. The shared video stream is previously stored in the system server 500 or real-timely transmitted (e.g., live broadcast) from the imaging device 600'.

It should be mentioned that although the present disclosure is described by using two VR boxes as an example, the present disclosure is not limited thereto. For example in the aspect that one imaging device (e.g., VR box II 600') is broadcasting streams to multiple VR boxes 600, each image viewing device includes a VR box and a wearable accessary respectively identical to the VR box 600 and the wearable accessary 400 as shown in FIGS. 18A and 18B. The user of each image viewing device uses the wearable accessary to control (by moving the wearable accessary in a predetermined pattern, gesture or direction) whether the stream from the system server 500 is shown on the VR box or the shared stream from the imaging device is shown on the VR box.

Briefly speaking, the image viewing devices in FIGS. 19A and 19B operate all functions as the image viewing devices in FIGS. 18A and 18B, respectively. The image viewing devices in FIGS. 19A and 19B are further arranged to show shared streams (including audio and video) shared from an imaging device 600' coupled to the internet to which the VR box 600 is coupled. Whether the shared streams are shown is controlled by a wearable accessary, e.g., moving in a predetermined direction, gesture or pattern to generate the control signal Scon. Furthermore, the VR box 600 may also be controlled by a pressing signal, a touch signal and/or a rotation signal of the wearable accessary 400 or the VR box 600 when a key thereon is pressed, a touch pad thereon detects a touch and/or a knob thereon is rotated to perform the switching between showing the streams (not shared from another imaging device) or the shared streams (shared from another imaging device). The definition of the streams and the shared streams have been described above and thus details thereof are not repeated herein.

It should be mentioned that although the present disclosure is described by a virtual reality system, the present disclosure is not limited thereto. In other aspects, the virtual reality system is replaced by an augmented reality system, a mobile computing device, or a device capable of acquiring images and sounds of an operation environment thereof.

As mentioned above, the present disclosure provides a biometric detection module (FIGS. 1A and 2A) and an operating method thereof (FIG. 8) that utilize the biometric characteristic as a reference for ID recognition and perform an individualized control according to the user ID so as to improve the applications of the biometric characteristic.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A virtual reality (VR) system, comprising:
an image viewing device, comprising:
  a VR box, configured to detect a biometric characteristic to identify a user ID according to the biometric characteristic, and output an ID signal associated with the identified user ID; and
a system server, coupled to the VR box, and configured to
  receive the ID signal from the VR box,
  receive shared video stream sharing from another VR box coupled to the system server via an internet, and transmit video stream associated with the identified user ID or the shared video stream to the VR box to be shown thereon; and a wearable accessary, configured to detect an attached status and movement of the wearable accessary after receiving the ID signal from the VR box, and send a control signal to the image viewing device to change image content to be shown on the VR box as the video stream or the shared video stream according to the detected movement of the wearable accessary when the attached status indicates continuous wearing.

2. The VR system as claimed in claim 1, wherein the wearable accessary is further configured to send a lock signal to the image viewing device to stop transmission of the video stream or the shared video stream when the attached status indicates a lift up state.

3. The VR system as claimed in claim 2, wherein the VR box is further configured to, after receiving the lock signal, identify another ID signal according to another biometric characteristic.

4. The VR system as claimed in claim 1, wherein the wearable accessary is a bracelet, a watch or a foot ring.

5. The VR system as claimed in claim 1, wherein the video stream is stored in the system server or download from a cloud or from a media platform, and the shared video stream is previously stored in the system server or real-timely transmitted from the another VR box.

6. The VR system as claimed in claim 1, wherein the detected movement is further configured to change at least one of a position and a viewing angle of the image content.

7. The VR system as claimed in claim 1, wherein the video stream is associated with at least one of video game, online meeting, online shopping and web tutorial, and the shared video stream is acquired by an imaging device of the another VR box.

8. The VR system as claimed in claim 1, wherein the biometric characteristic is selected from the group consisting of a fingerprint, an iris, a face, a voiceprint, an atrial fibrillation, a heart rate variability and a second derivative of photoplethysmogram.

9. A virtual reality (VR) system, comprising:

an image viewing device, comprising:

a VR box, configured to detect a biometric characteristic and output the biometric characteristic; and a system server, coupled to the VR box, and configured to receive the biometric characteristic to identify a user ID accordingly, receive shared video stream sharing from another VR box coupled to the system server via an internet, and transmit video stream associated with the identified user ID or the shared video stream to the VR box to be shown thereon; and a wearable accessary, configured to identify the user ID according to the biometric characteristic received from the VR box, detect an attached status and movement of the wearable accessary after confirming a valid user ID, and send a control signal to the image viewing device to change image content to be shown on the VR box as the video stream or the shared video stream according to the detected movement of the wearable accessary when the attached status indicates continuous wearing.

10. The VR system as claimed in claim 9, wherein the wearable accessary is further configured to send a lock signal to the image viewing device to stop transmission of the video stream or the shared video stream when the attached status indicates a lift up state.

11. The VR system as claimed in claim 10, wherein the VR box is further configured to, after receiving the lock signal, detect another biometric characteristic.

12. The VR system as claimed in claim 9, wherein the wearable accessary is a bracelet, a watch, or a foot ring.

13. The VR system as claimed in claim 9, wherein the video stream is stored in the system server or download from a cloud or from a media platform, and the shared video stream is previously stored in the system server or real-timely transmitted from the another VR box.

14. The VR system as claimed in claim 9, wherein the detected movement is further configured to change at least one of a position and a viewing angle of the image content.

15. The VR system as claimed in claim 9, wherein the video stream is associated with at least one of video game, online meeting, online shopping and web tutorial, and the shared video stream is acquired by an imaging device of the another VR box.

16. The VR system as claimed in claim 9, wherein the another VR box is previously identity authenticated with the VR system.

17. A virtual reality (VR) system, comprising:

an image viewing device, comprising:

a VR box, configured to identify a user ID and output an ID signal associated with the identified user ID, be coupled to an internet to receive shared video stream sharing from an imaging device connected to the internet, and show video stream associated with the identified user ID or the shared video stream thereon; and a wearable accessary, configured to detect movement of the wearable accessary after receiving the ID signal from the VR box, and send a control signal to the image viewing device to change image content to be shown on the VR box as the video stream or the shared video stream according to the detected movement of the wearable accessary.

18. The VR system as claimed in claim 17, wherein the wearable accessary is further configured to detect an attached status of the wearable accessary after receiving the ID signal from the VR box, and send a lock signal to the image viewing device to stop showing the video stream or the shared video stream on the VR box when the attached status indicates a lift up state.

19. The VR system as claimed in claim 17, wherein the imaging device is another VR box, a drone, a smartphone or a camera.

20. The VR system as claimed in claim 17, wherein the imaging device is previously identity authenticated with the VR system.

* * * * *